(12) United States Patent
Cho et al.

(10) Patent No.: US 8,148,402 B2
(45) Date of Patent: Apr. 3, 2012

(54) ISOINDOLINONE DERIVATIVES HAVING INHIBITORY ACTIVITY AGAINST T-TYPE CALCIUM CHANNEL AND METHOD FOR PREPARATION THEREOF

(75) Inventors: Yong Seo Cho, Seoul (KR); Ae Nim Pae, Seoul (KR); Hyunah Choo, Seoul (KR); Jae Kyun Lee, Seoul (KR); You Na Oh, Seoul (KR); Seon Hee Seo, Seoul (KR); Hyewhon Rhim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 626 days.

(21) Appl. No.: 12/256,701

(22) Filed: Oct. 23, 2008

(65) Prior Publication Data
US 2010/0004286 A1    Jan. 7, 2010

(30) Foreign Application Priority Data
Jul. 7, 2008    (KR) .................. 10-2008-0065522

(51) Int. Cl.
*A61K 31/445* (2006.01)
*C07D 401/02* (2006.01)
(52) U.S. Cl. ........................ 514/323; 546/201
(58) Field of Classification Search .................. 514/323; 546/201
See application file for complete search history.

(56) References Cited

FOREIGN PATENT DOCUMENTS
| | | |
|---|---|---|
| KR | 616099 | 3/2006 |
| KR | 743255 | 7/2007 |
| KR | 754325 | 8/2007 |
| KR | 784195 | 12/2007 |

OTHER PUBLICATIONS

Golub et al. Science (1999), vol. 286 531-537.*
Lala et al. Cancer and Metastasis Reviews (1998), 17(1), 91-106.*
Houman Khosravani, et al., Annals of Neurology (2005), 57, pp. 745-749.
Iuliia Vitko, et al., Journal of Neuroscience (May 11, 2005), 25(19), pp. 4844-4855.
Jean-Paul Clozel, et al., Cardiovascular Drugs and Therapy (1990), 4, pp. 731-736.
F. Hefti et al., Arzneimittelforschung (1990), 40, pp. 417-421.
Sven Moosmang, et al., Circulation Research (2006), 98 (1), pp. 105-110.
Sarah J.L. Flatters, Drugs of the Future (2005), 30(6), pp. 573-580.
Matthew E. Barton, et al., European Journal of Pharmacology (2005), 521, pp. 79-85.
Sarah J.L. Flatters, et al., Pain (2004), 109, pp. 150-161.
Ahmet Dogrul, et al., Pain (2003), 105 pp. 159-168.
Michael J. Berridge, et al., Nature Reviews Molecular Cell Biology (Jul. 2003), 4, pp. 517-529.

* cited by examiner

*Primary Examiner* — Rebecca Anderson
*Assistant Examiner* — Samantha Shterengarts
(74) *Attorney, Agent, or Firm* — Ladas & Parry LLP

(57) ABSTRACT

Disclosed are isoindolinone derivatives, represented by Chemical Formula 1, having inhibitory activity against T-type calcium channels, pharmaceutically acceptable salts thereof, a preparation method thereof, and a pharmaceutical composition comprising the same as an active ingredient.

[Chemical Formula 1]

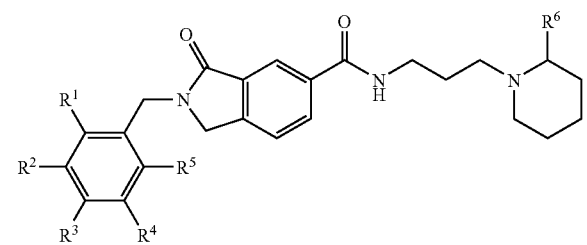

wherein $R^1$~$R^6$ are as defined in the specification.

6 Claims, No Drawings

ISOINDOLINONE DERIVATIVES HAVING INHIBITORY ACTIVITY AGAINST T-TYPE CALCIUM CHANNEL AND METHOD FOR PREPARATION THEREOF

BACKGROUND OF THE INVENTION

1. Field of the Invention

The present invention relates to isoindolinone derivatives having inhibitory activity against T-type calcium channels, pharmaceutically acceptable salts thereof, a method for the preparation thereof, and a pharmaceutical composition comprising the same as an active ingredient.

2. Description of the Related Art

A calcium channel is an ion channel with a selective permeability to the ion $Ca^{2+}$ which plays a privileged role in various intracellular signal transductions. These calcium channels are typically divided into high-voltage activated calcium channels and low-voltage activated calcium channels. Of the latter T-type calcium channels are representative. T-type calcium channels are found in the central nervous system, adrenal glomerulosa cells, the sinoatrial node, Purkinje cells of the heart and cardiac myocyte membranes. T-type calcium channel blockers are known to show the effective treatment of cerebral diseases, such as epilepsy, hypertension, etc., and heart diseases such as angina pectoris [1] Hosravani, Houman et al., "Effects of Cav3.2 channel mutations linked to idiopathic generalized epilepsy", *Annals of Neurology* (2005), 57(5), 745-749; 2) Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855; 3) Clozel, *Cardiovas Drugs Ther.* (1990), 4, pp. 731-736; 4) Hefti, *Arzneimittelforschung* (1990), 40, 417-421; 5) Moosmang, Sven et al., "Antihypertensive Effects of the Putative T-Type Calcium Channel Antagonist Mibefradil Are Mediated by the L-Type Calcium Channel Cav1. 2", *Circulation Research* (2006), 98(1), 105-110]. Recently, T-type calcium channel blockers have been reported to have therapeutic effects on chronic pains [*Drugs of the Future* (2005), 30(6), 573-580]. For example, the T-type calcium channel blockers mibefradil and ethosuximide were shown to inhibit mechanically and thermally induced pain in a dose-dependent manner in a spinal nerve ligation model, indicating that T-type calcium channel blockers are useful in the treatment of neuropathic pain [1) Barton, Matthew E. et al., "The antihyperalgesic effects of the T-type calcium channel blockers ethosuximide, trimethadione, and mibefradil", *European Journal of Pharmacology* (2005), 521, 79-85; 2) Flatters, Sarah J. L., "T-type calcium channels: A potential target for the treatment of chronic pain", *Drugs of the Future* (2005), 30(6), 573-580; 3) Flatters, Sarah J. L. et al., "Ethosuximide reverses paclitaxel- and vincristine-induced painful peripheral neuropathy", *Pain* (2004), 109, 150-161; 4) Dogrul, Ahmet et al., "Reversal of experimental neuropathic pain by T-type calcium channel blockers", *Pain* (2003), 105, 159-168]. In addition, calcium, serving as a messenger of signal transduction, regulates various cellular functions. Since cell growth is among the cellular functions in which calcium is involved, it is expected that T-type calcium channel blockers show anti-cancer effects [Nat. Rev. Mol. Cell Biol. 2003, 4, 517-529].

Mibefradil, belonging to a group known as T-type calcium channel blockers, has recently been a drug for the treatment of hypertension and chronic angina pectoris, but is now prohibited from being marketed due to the potential for drug interactions, some of them serious, which may occur which it is taken together with certain other medications. Therefore, there is an imperative requirement for the development of a novel T-type calcium channel blocker.

In spite of extensive efforts, selective T-type calcium channel blockers have rarely been developed. Compounds capable of functioning as T-type calcium channel blockers are disclosed in Korean Patent Nos. 784,195 and 754,325 with a backbone of quinazoline therefor, in Korean Patent No. 616,099 with a backbone of isoxazole therefor, and in Korean Patent No. 743,255 with a backbone of 1,3-dioxoisoindone therefor.

However, there is still a need for selective T-cell calcium channel blockers that show properties in terms of pharmacokinetic profile and ADME (absorption, distribution, metabolism and excretion) disposition and are useful in the treatment of relevant diseases, such as hypertension, cancer, epilepsy and neuropathic pain.

SUMMARY OF THE INVENTION

Accordingly, the present invention has been made keeping in mind the above problems occurring in the prior art, and an object of the present invention is to provide novel isoindolinone derivatives or pharmaceutically acceptable salts thereof which can effectively inhibit the activity of T-type calcium channels.

It is another object of the present invention to provide a method for preparing the isoindolinone derivatives.

It is a further object of the present invention to provide a pharmaceutical composition inhibitory of the activity of T-type calcium channel, comprising the isoindolinone derivatives or pharmaceutically acceptable salts thereof as an active ingredient.

It is still a further object of the present invention to provide a pharmaceutical composition for the treatment of hypertension, cancer, epilepsy, and neuropathic pain.

In order to accomplish the above objects, the present invention provides novel isoindolinone derivatives or pharmaceutically acceptable salt thereof as T-type calcium channel blockers.

Also, the present invention provides a method for preparing the isoindolinone derivatives, comprising the amidation of isoindolinone carboxylic acid derivatives having benzyl substituents with piperidinyl amine derivatives.

Further, the present invention provides a pharmaceutical composition showing inhibitory activity against T-type calcium channel, comprising the isoindolinone derivatives or pharmaceutically acceptable salts thereof as an active ingredient.

In addition, the present invention provides a pharmaceutical composition for the treatment of hypertension, cancer, epilepsy, and neuropathic pain, comprising the isoindolinone derivatives or pharmaceutically acceptable salts thereof as an active ingredient.

DESCRIPTION OF THE PREFERRED EMBODIMENTS

In accordance with an aspect thereof, the present invention pertains to an isoindolinone derivative, represented by the following Chemical Formula 1, or a pharmaceutically acceptable salt thereof.

[Chemical Formula 1]

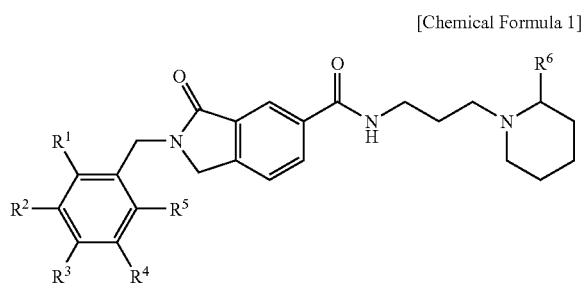

wherein, $R^1$~$R^5$ represent independently a hydrogen atom, a halogen atom, a $C_1$~$C_6$ alkoxy, a $C_1$~$C_6$ alkyl, a $C_1$~$C_6$ haloalkyl, a nitro, a cyano or a hydroxy; and $R^6$ represents a hydrogen atom, a $C_1$~$C_6$ alkyl, or an aryl.

The details are given of the substituents of the isoindolinone derivatives represented by Chemical Formula 1. The term "alkyl", as used herein, is intended to refer to a straight, branched or cyclic carbon chain containing one to six carbon atoms, examples of which include methyl, ethyl, normal propyl, isopropyl, normal butyl, isobutyl, tert-butyl, cyclopentyl, and cyclohexyl. The term "haloalkyl", as used herein, is intended to refer to a straight, branched or cyclic carbon chain containing one to six carbon atoms, with 1 to 13 of the halogen atoms fluorine, chlorine, bromine and/or iodine substituted thereto, be it representatively fluoromethyl, trifluoromethyl, 1,2-dichloroethyl, 1,1-dichloroethyl, pentafluoroethyl, etc. As used herein, the term "alkoxy" means an alkyl (as defined above) group linked to oxygen. The term "aryl", as used herein, is intended to denote any functional group or substituent derived from one planar set of six carbon atoms or two or more planar sets of at least ten carbon atoms that are connected by delocalized electrons numbering the same as if they consisted of alternating single and double covalent bonds, be it phenyl, naphthyl, etc. The aryl may contain at least one substituent selected from among halogen atoms, alkyl, alkoxy, phenoxy, etc. The term "benzyl", as used herein, is intended to describe a benzene ring with one methylene carbon connected as a substituent thereto.

In a preferred embodiment of the isoindolinone derivative represented by Chemical Formula 1, $R^1$~$R^5$ is a hydrogen atom or a halogen atom selected from among a fluorine atom, a chlorine atom, a bromine atom, an iodine atom and a combination thereof; and $R^6$ is a hydrogen atom, a methyl, a ethyl, a normal propyl, an isopropyl, a normal butyl, a tert-butyl or a phenyl.

Concrete examples of the isoindolinone derivatives represented by Chemical Formula 1 include:

Compound 1: 2-benzyl-3-oxo-N-(3-(piperidin-1-yl)propyl)isoindoline-5-carboxamide;
Compound 2: 2-(3-fluorobenzyl)-3-oxo-N-(3-(piperidin-1-yl)propyl)isoindoline-5-carboxamide;
Compound 3: 2-(4-fluorobenzyl)-3-oxo-N-(3-(piperidin-1-yl)propyl)isoindoline-5-carboxamide;
Compound 4: 2-(3-chlorobenzyl)-3-oxo-N-(3-(piperidin-1-yl)propyl)isoindoline-5-carboxamide;
Compound 5: 2-(4-chlorobenzyl)-3-oxo-N-(3-(piperidin-1-yl)propyl)isoindoline-5-carboxamide;
Compound 6: 2-(3-bromobenzyl)-3-oxo-N-(3-(piperidin-1-yl)propyl)isoindoline-5-carboxamide;
Compound 7: 2-(4-bromobenzyl)-3-oxo-N-(3-(piperidin-1-yl)propyl)isoindoline-5-carboxamide;
Compound 8: 2-(3-iodobenzyl)-3-oxo-N-(3-(piperidin-1-yl)propyl)isoindoline-5-carboxamide;
Compound 9: 2-(4-iodobenzyl)-3-oxo-N-(3-(piperidin-1-yl)propyl)isoindoline-5-carboxamide;
Compound 10: 2-benzyl-N-(3-(2-methylpiperidin-1-yl)propyl)-3-oxoisoindoline-5-carboxamide;
Compound 11: 2-(3-fluorobenzyl)-N-(3-(2-methylpiperidin-1-yl)propyl)-3-oxoisoindoline-5-carboxamide;
Compound 12: 2-(4-fluorobenzyl)-N-(3-(2-methylpiperidin-1-yl)propyl)-3-oxoisoindoline-5-carboxamide;
Compound 13: 2-(3-chlorobenzyl)-N-(3-(2-methylpiperidin-1-yl)propyl)-3-oxoisoindoline-5-carboxamide;
Compound 14: 2-(4-chlorobenzyl)-N-(3-(2-methylpiperidin-1-yl)propyl)-3-oxoisoindoline-5-carboxamide;
Compound 15: 2-(3-bromobenzyl)-N-(3-(2-methylpiperidin-1-yl)propyl)-3-oxoisoindoline-5-carboxamide;
Compound 16: 2-(4-bromobenzyl)-N-(3-(2-methylpiperidin-1-yl)propyl)-3-oxoisoindoline-5-carboxamide;
Compound 17: 2(3-iodobenzyl)-N-(3-(2-methylpiperidin-1-yl)propyl)-3-oxoisoindoline-5-carboxamide;
Compound 18: 2-(4-iodobenzyl)-N-(3-(2-methylpiperidin-1-yl)propyl)-3-oxoisoindoline-5-carboxamide;
Compound 19: 2-benzyl-N-(3-(2-ethylpiperidin-1-yl)propyl)-3-oxoisoindoline-5-carboxamide;
Compound 20: N-(3-(2-ethylpiperidin-1-yl)propyl)-2-(3-fluorobenzyl)-3-oxoisoindoline-5-carboxamide;
Compound 21: N-(3-(2-ethylpiperidin-1-yl)propyl)-2-(4-fluorobenzyl)-3-oxoisoindoline-5-carboxamide;
Compound 22: 2-(3-chlorobenzyl)-N-(3-(2-ethylpiperidin-1-yl)propyl)-3-oxoisoindoline-5-carboxamide;
Compound 23: 2-(4-chlorobenzyl)-N-(3-(2-ethylpiperidin-1-yl)propyl)-3-oxoisoindoline-5-carboxamide;
Compound 24: 2-(3-bromobenzyl)-N-(3-(2-ethylpiperidin-1-yl)propyl)-3-oxoisoindoline-5-carboxamide;
Compound 25: 2-(4-bromobenzyl)-N-(3-(2-ethylpiperidin-1-yl)propyl)-3-oxoisoindoline-5-carboxamide;
Compound 26: N-(3-(2-ethylpiperidin-1-yl)propyl)-2-(3-iodobenzyl)-3-oxoisoindoline-5-carboxamide;
Compound 27: N-(3-(2-ethylpiperidin-1-yl)propyl)-2-(4-iodobenzyl)-3-oxoisoindoline-5-carboxamide;
Compound 28: 2-benzyl-3-oxo-N-(3-(2-propylpiperidin-1-yl)propyl)isoindoline-5-carboxamide;
Compound 29: 2-(3-fluorobenzyl)-3-oxo-N-(3-(2-propylpiperidin-1-yl)propyl)isoindoline-5-carboxamide;
Compound 30: 2-(4-fluorobenzyl)-3-oxo-N-(3-(2-propylpiperidin-1-yl)propyl)isoindoline-5-carboxamide;
Compound 31: 2-(3-chlorobenzyl)-3-oxo-N-(3-(2-propylpiperidin-1-yl)propyl)isoindoline-5-carboxamide;
Compound 32: 2-(4-chlorobenzyl)-3-oxo-N-(3-(2-propylpiperidin-1-yl)propyl)isoindoline-5-carboxamide;
Compound 33: 2-(3-bromobenzyl)-3-oxo-N-(3-(2-propylpiperidin-1-yl)propyl)isoindoline-5-carboxamide;
Compound 34: 2-(4-bromobenzyl)-3-oxo-N-(3-(2-propylpiperidin-1-yl)propyl)isoindoline-5-carboxamide;
Compound 35: 2-(3-iodobenzyl)-3-oxo-N-(3-(2-propylpiperidin-1-yl)propyl)isoindoline-5-carboxamide;
Compound 36: 2-(4-iodobenzyl)-3-oxo-N-(3-(2-propylpiperidin-1-yl)propyl)isoindoline-5-carboxamide;
Compound 37: 2-benzyl-N-(3-(2-isopropylpiperidin-1-yl)propyl)-3-oxoisoindoline-5-carboxamide;
Compound 38: 2-(3-fluorobenzyl)-N-(3-(2-isopropylpiperidin-1-yl)propyl)-3-oxoisoindoline-5-carboxamide;
Compound 39: 2-(4-fluorobenzyl)-N-(3-(2-isopropylpiperidin-1-yl)propyl)-3-oxoisoindoline-5-carboxamide;
Compound 40: 2-(3-chlorobenzyl)-N-(3-(2-isopropylpiperidin-1-yl)propyl)-3-oxoisoindoline-5-carboxamide;
Compound 41: 2-(4-chlorobenzyl)-N-(3-(2-isopropylpiperidin-1-yl)propyl)-3-oxoisoindoline-5-carboxamide;

Compound 42: 2-(3-bromobenzyl)-N-(3-(2-isopropylpiperidin-1-yl)propyl)-3-oxoisoindoline-5-carboxamide;
Compound 43: 2-(4-bromobenzyl)-N-(3-(2-isopropylpiperidin-1-yl)propyl)-3-oxoisoindoline-5-carboxamide;
Compound 44: 2-(3-iodobenzyl)-N-(3-(2-isopropylpiperidin-1-yl)propyl)-3-oxoisoindoline-5-carboxamide;
Compound 45: 2-(4-iodobenzyl)-N-(3-(2-isopropylpiperidin-1-yl)propyl)-3-oxoisoindoline-5-carboxamide;
Compound 46: 2-benzyl-N-(3-(2-butylpiperidin-1-yl)propyl)-3-oxoisoindoline-5-carboxamide;
Compound 47: N-(3-(2-butylpiperidin-1-yl)propyl)-2-(3-fluorobenzyl)-3-oxoisoindoline-5-carboxamide;
Compound 48: N-(3-(2-butylpiperidin-1-yl)propyl)-2-(4-fluorobenzyl)-3-oxoisoindoline-5-carboxamide;
Compound 49: N-(3-(2-butylpiperidin-1-yl)propyl)-2-(3-chlorobenzyl)-3-oxoisoindoline-5-carboxamide;
Compound 50: N-(3-(2-butylpiperidin-1-yl)propyl)-2-(4-chlorobenzyl)-3-oxoisoindoline-5-carboxamide;
Compound 51: 2-(3-bromobenzyl)-N-(3-(2-butylpiperidin-1-yl)propyl)-3-oxoisoindoline-5-carboxamide;
Compound 52: 2-(4-bromobenzyl)-N-(3-(2-butylpiperidin-1-yl)propyl)-3-oxoisoindoline-5-carboxamide;
Compound 53: N-(3-(2-butylpiperidin-1-yl)propyl)-2-(3-iodobenzyl)-3-oxoisoindoline-5-carboxamide;
Compound 54: N-(3-(2-butylpiperidin-1-yl)propyl)-2-(4-iodobenzyl)-3-oxoisoindoline-5-carboxamide;
Compound 55: 2-benzyl-3-oxo-N-(3-(2-phenylpiperidin-1-yl)propyl)isoindoline-5-carboxamide;
Compound 56: 2-(3-fluorobenzyl)-3-oxo-N-(3-(2-phenylpiperidin-1-yl)propyl)isoindoline-5-carboxamide;
Compound 57: 2-(4-fluorobenzyl)-3-oxo-N-(3-(2-phenylpiperidin-1-yl)propyl)isoindoline-5-carboxamide;
Compound 58: 2-(3-chlorobenzyl)-3-oxo-N-(3-(2-phenylpiperidin-1-yl)propyl)isoindoline-5-carboxamide;
Compound 59: 2-(4-chlorobenzyl)-3-oxo-N-(3-(2-phenylpiperidin-1-yl)propyl)isoindoline-5-carboxamide;
Compound 60: 2-(3-bromobenzyl)-3-oxo-N-(3-(2-phenylpiperidin-1-yl)propyl)isoindoline-5-carboxamide;
Compound 61: 2-(4-bromobenzyl)-3-oxo-N-(3-(2-phenylpiperidin-1-yl)propyl)isoindoline-5-carboxamide;
Compound 62: 2-(3-iodobenzyl)-3-oxo-N-(3-(2-phenylpiperidin-1-yl)propyl)isoindoline-5-carboxamide; and
Compound 63: 2-(4-iodobenzyl)-3-oxo-N-(3-(2-phenylpiperidin-1-yl)propyl)isoindoline-5-carboxamide.

The isoindolinone derivatives according to the present invention, represented by chemical formula 1, may be used in the form of pharmaceutically acceptable salts. For example, Within the range of these salts are included acid addition salts formed with pharmaceutically acceptable free acids. Useful as the free acids are non-toxic inorganic acids such as hydrochloric acid, bromic acid, sulfonic acid, aminosulfuric acid, phosphoric acid, nitric acid, etc., and non-toxic organic acids such as acetic acid, propionic acid, succinic acid, glycolic acid, stearic acid, lactic acid, tartaric acid, citric acid, para-toluenesulfonic acid, methanesulfonic acid, etc.

It should be understood that in addition to the isoindolinone derivatives of chemical formula 1 and pharmaceutically acceptable salts thereof, solvates, hydrates and racemates that can be prepared therefrom are included within the scope of the present invention.

The acid addition salts of the compounds according to the present invention may be prepared using a typical method, for example, by dissolving the compound of chemical formula 1 in excess acid in water and precipitating the resulting salt in a water-miscible organic solvent, e.g., acetone, methanol, ethanol, or acetonitrile. Alternatively, the compounds of chemical formula 1 may be heated along with the same amount of acid or alcohol in water, followed by evaporating the mixture and drying or suction filtering the precipitate to prepare acid addition salts thereof.

In accordance with another aspect thereof, the present invention pertains to a method for preparing the isoindolinone derivative of Chemical Formula 1, as illustrated by the following Reaction Scheme 1, comprising:

converting 3-bromo-4-methylbenzoic acid of Chemical Formula 2 into aryl lithium using methylmagnesium bromide ($CH_3MgBr$) and n-butyl lithium in a nitrogen atmosphere, followed by the carboxylation of aryl lithium with carbon dioxide into a dicarboxylic acid compound of Chemical Formula 3 (Step 1);

esterifying the dicarboxylic acid of Chemical Formula 3 with an alkyl to give a diester of Chemical Formula 4 (Step 2);

brominating the diester of Chemical Formula 4 into a bromine compound of Chemical Formula 5 (Step 3);

subjecting the brominated compound of Chemical Formula 5 to $SN_2$-type alkylation with a benzylamine of Chemical Formula 6, followed by cyclization to afford an isoindolinone backbone compound of Chemical Formula 7 (Step 4);

hydrolyzing the compound of Chemical Formula 7 to an isoindolinone carboxylic acid derivative of Chemical Formula 8 (Step 5); and amide-coupling the isoindolinone carboxylic acid derivative of Chemical Formula 8 with a piperidinyl propylamine derivative of Chemical Formula 9 to afford the isoindolinone derivative of Chemical Formula 1 (Step 6).

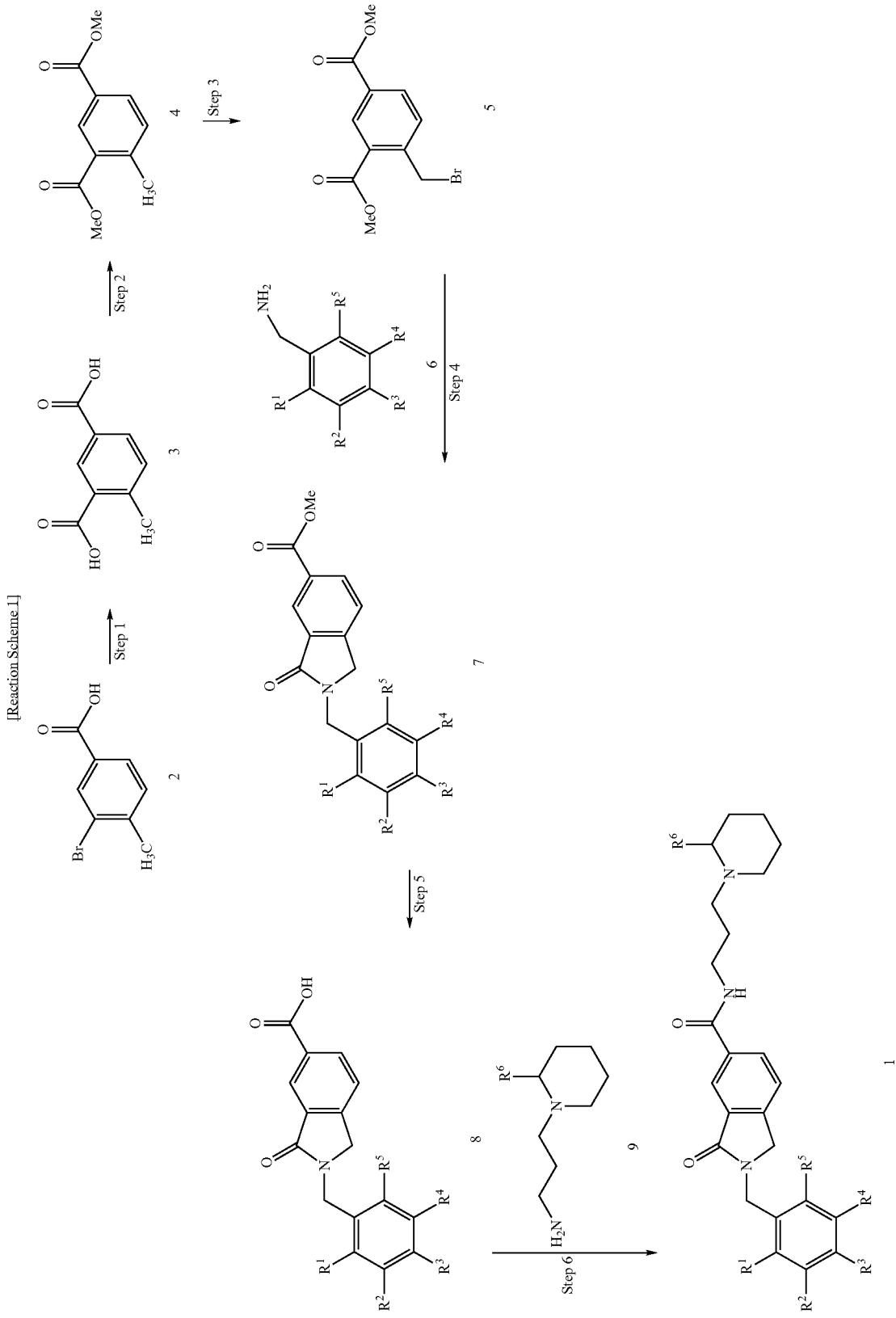

wherein, $R^1$~$R^6$ are as defined in Chemical Formula 1.

The details are given of the preparation method according to the present invention, below.

First, 3-bromo-4-methylbenzoic acid, represented by Chemical Formula 2, is reacted with methylmagnesium bromide ($CH_3MgBr$) and n-butyl lithium under nitrogen atmosphere to produce an aryl lithium which is then carboxylated with carbon dioxide to the dicarboxylic acid of Chemical Formula 3 (Step 1). That is, to a solution of the 3-bromo-4-methylbenzoic acid of Chemical Formula 2 in a polar organic solvent such as tetrahydrofuran is added methylmagnesium bromide ($CH_3MgBr$) at a temperature from $-20°$ C. to $20°$ C., followed by the slow dropwise addition of n-butyl lithium at a temperature from $-80°$ C. to $-60°$ C. After the completion of the addition, the reaction solution is heated to room temperature to terminate the reaction.

Subsequently, the dicarboxylic acid of Chemical Formula 3 is esterified with alcohol in the presence of an acid such as sulfuric acid to give the diester of Chemical Formula 4 (Step 2). For example, the dicarboxylic acid of Chemical Formula 3 is dissolved in an alcohol such as methanol and subjected to alkyl esterification in the presence of an acid such as sulfuric acid under a reflux condition.

Afterwards, bromination with N-bromosuccinimide (NBS) is conducted on the diester of Chemical Formula 4 to give a brominated compound of Chemical Formula 5 (Step 3). For example, the diester of Chemical Formula 4 is dissolved in an organic solvent such as dichloromethane and then treated with a bromination reagent such as N-bromosuccinimide (NBS) in the presence of benzoic peroxyanhydride under a reflux condition.

Thereafter, the brominated compound of Chemical Formula 5 is submitted to $SN_2$-type alkylation with the benzylamine of Chemical Formula 6, followed by cyclization to afford the isoindolinone of Chemical Formula 7 (Step 4). The alkylation and the cyclization are performed in series preferably at a temperature from $80°$ C. to $150°$ C. in the presence of a base such as mono-, di- or trialkyl amine.

Next, the compound of Chemical Formula 7 is hydrolyzed to an inoindolinone carboxylic acid derivative of Chemical Formula 8 in the presence of hydroxide ($OH^-$) (Step 5). The hydrolysis is conducted in a typical manner. For example, the hydrolysis reaction is conducted in an organic solvent containing water using lithium hydroxide (LiOH) under a mild condition such as at room temperature.

Finally, the isoindolinone carboxylic acid derivative of Chemical Formula 8 undergoes amide coupling with a piperidinyl propyl amine derivative of Chemical Formula 9 to produce the isoindolinone derivative of Chemical Formula 9 (Step 6). This amide coupling is conducted at around room temperature from $20°$ C. to $30°$ C. in a solvent selected from among dichloromethane, dimethylformamide (DMF), dimethylacetamide (DMAc) and dioxane using 1-ethyl-3-(3'-dimethylaminopropyl)carbdiimide hydrochloride (EDCI) and hydroxy-1H-benzotriazole (HOBT).

For use in the preparation method according to the present invention, the 3-bromo-4-methylbenzoic acid of Chemical Formula 2 serving as the starting material, and the benzylamine of Chemical Formula 6 are known in the art and are commercially available. The piperidinyl propylamine derivative of Chemical Formula 9 is also known in the art and may be readily prepared according to literature.

In accordance with a further aspect thereof, the present invention pertains to a pharmaceutical composition comprising the isoindolinone derivative of Chemical Formula 1 or a pharmaceutically acceptable salt thereof as an active ingredient.

In accordance with a further aspect thereof, the present invention pertains to a method for treatment of a disease caused by activity of a T-type calcium channel, comprising administering the isoindolinone derivative of Chemical Formula 1 or the pharmaceutically acceptable salt in a therapeutically effective amount to a subject in need thereof.

T-type calcium channels exist in the central nervous system, adrenal glomerulosa cells, the sinoatrial node, Purkinje cells of the heart and cardiac myocyte membranes. T-type calcium channel blockers are known to be effective for treatment of cerebral diseases, such as epilepsy, hypertension, etc., and heart diseases such as angina pectoris [1) Hosravani, Houman et al., "Effects of Cav3.2 channel mutations linked to idiopathic generalized epilepsy", *Annals of Neurology* (2005), 57(5), 745-749; 2) Vitko, Iuliia et al., "Functional characterization and neuronal modeling of the effects of childhood absence epilepsy variants of CACNA1H, a T-type calcium channel", *Journal of Neuroscience* (2005), 25(19), 4844-4855; 3) Clozel, *Cardiovas Drugs Ther*. (1990), 4, pp. 731-736; 4) Hefti, *Arzneimittelforschung* (1990), 40, 417-421; 5) Moosmang, Sven et al., "Antihypertensive Effects of the Putative T-Type Calcium Channel Antagonist Mibefradil Are Mediated by the L-Type Calcium Channel Cav1. 2", *Circulation Research* (2006), 98(1), 105-110]. Also, T-type calcium channel blockers have recently been reported to be useful in the treatment of chronic pain [*Drugs of the Future* (2005), 30(6), 573-580].

Calcium, serving as a messenger of signal transduction, regulates various cellular functions. Since cell growth is among the cellular functions in which calcium is involved, it is expected that T-type calcium channel blockers will show anti-cancer effects [Nat. Rev. Mol. Cell Biol. 2003, 4, 517-529].

Experiments with the HEK293 cell line showed that the isoindolinone derivative or the pharmaceutically acceptable salt thereof useful as an active ingredient of the pharmaceutical composition in accordance with the present invention significantly suppresses calcium ions from flowing via T-type calcium channels (refer to Experimental Examples and Table 2, below). Thus, with the ability to effectively inhibit the activity of T-type calcium channels, the pharmaceutical composition according to the present invention can be used as a preventative of or a therapeutic for the diseases caused by the hyper-activity of T-type calcium channels, such as hypertension, cancer, epilepsy, neuropathic pain, etc.

For clinical practice, the pharmaceutical composition in accordance with the present invention may be used in oral or non-oral forms. It is usually formulated in combination with a carrier, an excipient or a diluent. Oral dosage preparations of the compounds of the present invention may take the form of tablets, capsules, solutions, syrups, suspensions, and the like. Non-oral dosage forms may be injections via intraperitoneal, subcutaneous, intramuscular, or transdermal routes.

The active ingredient, acting as a T-type calcium channel blocker, according to the present invention may be administered at a daily dose ranging from 0.01 to 1,000 mg/kg of body weight of adults. The effective dosage of the active ingredient in accordance with the present invention depends on various factors, including the patient's age, weight, gender, route of administration, state of health, severity of diseases, etc. The compound may be administered in a single dose or may be divided into three doses per day according to the instructions of a physician or pharmacist.

A better understanding of the present invention may be obtained through the following examples which are set forth to illustrate, but are not to be construed as limiting the present invention.

EXAMPLE

Preparation of 2-Benzyl-3-oxo-N-(3-(piperidin-1-yl)propyl)isoindoline-5-carboxamide (Chemical Formula 1)

Step 1: Synthesis of 4-Methyl isophthalic acid (Chemical Formula 3)

Under nitrogen atmosphere, 3-bromo-4-methylbenzoic acid (Chemical Formula 2) (5 g, 23.3 mmol) was dissolved in THF, and to this solution was dropwise added methylmagnesium bromide in a 3.0 M diethylether solution (8.5 ml, 25.6 mmol) at 0° C. with stirring. The resulting solution was cooled to −65° C. and then n-butyl lithium in a 1.6M hexane solution (29 ml, 46.5 mmol) were added thereto, followed by stirring for 3 hours. The temperature of the reaction solution was elevated to −40° C., and then to room temperature in the presence of dry ice with stirring. The reaction process was monitored with TLC [$CH_2Cl_2$:MeOH=4:1]. When the reaction was detected to have gone to completion, saturated $NH_4Cl$ was added to the reaction mixture, followed by extraction with ethyl acetate. The aqueous layer thus obtained was adjusted into pH 1 with 1N HCl before additional extraction with ethyl acetate. The organic layer thus formed was dried over anhydrous $MgSO_4$, filtered, and concentrated in vacuo to afford 4-methylisophthalic acid (Chemical Formula 3) (Yield 95%)

$^1$H NMR (400 MHz, $CDCl_3$) δ 8.52 (s, 1H), 8.03 (d, 1H, J=8.0 Hz), 7.40 (d, 1H, J=6.7 Hz), 2.64 (s, 3H)

Step 2: Synthesis of dimethyl 4-methylisophthalate (Chemical Formula 4)

Under nitrogen atmosphere, conc. sulfuric acid (4 mL) was added to a solution of 4-methylisophthalic acid (Chemical Formula 3) (5 g, 27.8 mmol) in methanol (120 mL) and the solution was fluxed at 80° C. for 24 hours. The reaction progress was monitored using TLC [Hex: EA=1:1]. When the reaction was completed, the solvent was evaporated and saturated $NaHCO_3$ was added, followed by extraction with $CHCl_3$. The organic layer thus obtained was dried over anhydrous $MgSO_4$, filtered and concentrated in vacuo. The purification of the concentrate through column chromatography [Hexane: EtOAc=5:1] afforded 0.68 g of dimethyl 4-methylisophthalate (Chemical Formula 4) (Yield 74%).

$^1$H NMR (400 MHz, $CDCl_3$) δ 8.57 (s, 1H), 8.05 (d, 1H, J=8.0 Hz), 7.33 (d, 1H, J=8.0 Hz), 3.93 (s, 3H), 3.92 (s, 3H), 2.67 (s, 3H)

Step 3: Synthesis of dimethyl 4-(bromomethyl)isophthlate (Chemical Formula 5)

To a solution of dimethyl 4-methylisophthlate (Chemical Formula 4) (4 g, 19.2 mmol) in distilled dichloromethane were added N-bromosuccinimide (NBS, 4.8 g, 26.9 mmol) and benzoic peroxyanhydride (0.47 g, 19.2 mmol), followed by reaction at 80° C. for 24 hours in a pressure vessel with constant stirring. The reaction progress was monitored by TLC [Hex:EA=3:1]. When the reaction was detected to have reached completion, saturated $NaHCO_3$ was added to the reaction mixture, followed by extraction with dichloromethane. The organic layer thus formed was dried over anhydrous $MgSO_4$, filtered and concentrated in a vacuum. The purification of the concentrate through column chromatography [Hexane: EtOAc=20:1] produced 4 g of dimethyl 4-(bromomethyl)isophthalate (Chemical Formula 5) (70%).

$^1$H NMR (400 MHz, $CDCl_3$) δ 8.61 (s, 1H), 8.13 (d, 1H, J=8.0 Hz), 7.55 (d, 1H, J=8.0 Hz), 5.00 (s, 2H), 3.97 (s, 3H), 3.95 (s, 3H)

Step 4: Synthesis of methyl 2-benzyl-3-oxoisoindoline-5-carboxylate (Chemical Formula 7)

To a solution of dimethyl 4-(bromomethyl)isophthalate (Chemical Formula 5) (1 g, 3.48 mmol) in toluene were added triethyl amine (1.46 ml, 10.4 mmol) and benzyl amine (0.38 ml, 3.48 mmol) and the reaction was proceeded at 110° C. for 3-4 hours in a pressure vessel with stirring. Monitoring of the reaction progress was done with TLC [Hex: EA=1:1]. When the reaction was completed, extraction was performed sequentially with ethylacetate and $H_2O$, a saturated aqueous $NaHCO_3$ solution, a 10% aqueous $KHSO_4$ solution, and an aqueous NaCl solution in that order, and the organic layer thus obtained was dried over anhydrous $MgSO_4$, filtered and concentrated in a vacuum. The purification of the concentrate through column chromatography [Hexane: EtOAc=3:1] afforded 0.69 g of methyl 2-benzyl-3-oxoisoindoline-5-carboxylate (Chemical Formula 7) (70%).

$^1$H NMR (400 MHz, $CDCl_3$) δ 8.56 (s, 1H), 8.22 (d, 1H, J=8.0 Hz), 7.46 (d, 1H, J=8.0 Hz), 7.30-7.35 (m, 5H), 4.82 (s, 2H), 4.32 (s, 2H), 3.97 (s, 3H)

Step 5: Synthesis of 2-benzyl-3-oxoisoindoline-5-carboxylic acid (Chemical Formula 8)

LiOH.$H_2O$ (0.30 g, 7.11 mmol) was added to a solution of methyl 2-benzyl-3-oxoisoindoline-5-carboxylate (Chemical Formula 7) (0.5 g, 1.78 mmol) in a mixture of 3:1:1(v/v/v) THF:methanol:$H_2O$ which was then stirred for 1 hour. The reaction progress was monitored using TLC [Hex:EA=1:1]. When the reaction was completed, the pH of the reaction mixture was adjusted to 4 with 1N HCl, followed by extraction with ethyl acetate. The organic layer thus obtained was dried over anhydrous $MgSO_4$, filtered and concentrated in a vacuum to afford 2-benzyl-3-oxoisoindoline-5-carboxylic acid (Chemical Formula 8) at a yield of 85%.

$^1$H NMR (400 MHz, DMSO-$d_6$) δ 13.17 (s, 1H), 8.18 (s, 1H), 8.14 (d, 1H, J=8.0 Hz), 7.67 (d, 1H, J=8.0 Hz), 7.21-7.36 (m, 5H), 4.73 (s, 2H), 4.44 (s, 2H)

Step 6: Synthesis of 2-benzyl-3-oxo-N-(3-(piperidin-1-yl)propyl)isoindoline-5-carboxamide (Chemical Formula 1)

Under nitrogen atmosphere, 2-benzyl-3-oxoisoindoline-5-carboxylic acid (Chemical Formula 8) (100 mg, 0.374 mmol), 1-ethyl-3-(3'-dimethylaminopropyl)carbodiimide hydrochloride (EDCI, 0.144 g, 0.749 mmol), and 1-hydroxybenzotriazole (HOBT, 0.025 g, 0.187 mmol) were reacted at room temperature in distilled dichloromethane, with stirring, for 2 hours. After monitoring through TLC [$CH_2Cl_2$:MeOH=4:1], the temperature was decreased to −40° C. at which time 3-(piperidin-1-yl)propan-1-amine (80 μL, 0.562 mmol) was added before stirring for 3-4 hours. The reaction progress was monitored with TLC [Hex: EA=1:1]. When the reaction was completed, the reaction mixture was extracted with $NaHCO_3$ and then with $CH_2Cl_2$. The organic layer thus obtained was dried over anhydrous $MgSO_4$ and filtered. The filtrate was concentrated in a vacuum and the concentrate was purified using column chromatography [CH₂Cl₂:MeOH=20:1] to afford 2-benzyl-3-oxo-N-(3-(piperidin-1-yl)propyl)isoindoline-5-carboxamide (Chemical Formula 1) in an amount of 96 mg (Yield 73%). This product was solidified with ethereal HCl to give a hydrochloride.

¹H NMR (400 MHz, CDCl₃) δ 8.85 (s, 1H), 8.30 (s, 1H), 8.14 (d, 1H, J=8.0 Hz), 7.42 (d, 1H, J=7.8 Hz), 7.26-7.35 (m, 5H), 4.80 (s, 2H), 4.28 (s, 2H), 3.59 (q, 2H, J=5.4 Hz) 2.66 (t, 2H, J=5.7 Hz), 2.59 (s, 4H), 1.85-1.91 (m, 2H), 1.70-1.91 (m, 4H), 1.53 (s, 2H)

The compounds of Chemical Formula 1 prepared using the method described in the Example are summarized in Table 1, below, together with the spectrometric data thereof.

TABLE 1

| Cpd Nos | Compounds | ¹H NMR |
|---|---|---|
| 1 | 2-benzyl-3-oxo-N-(3-(piperidin-1-yl)propyl)isoindoline-5-carboxamide | ¹H NMR (400 MHz, CDCl₃) δ 8.85 (s, 1H), 8.30 (s, 1H), 8.14 (d, 1H, J = 8.0 Hz), 7.42 (d, 1H, J = 7.8 Hz), 7.26-7.35 (m, 5H), 4.80 (s, 2H), 4.28 (s, 2H), 3.59 (q, 2H, J = 5.4 Hz), 2.66 (t, 2H, J = 5.7 Hz), 2.59 (s, 4H), 1.85-1.91 (m, 2H), 1.70-1.91 (m, 4H), 1.53 (s, 2H) |
| 2 | 2-(3-fluorobenzyl)-3-oxo-N-(3-(piperidin-1-yl)propyl)isoindoline-5-carboxamide | ¹H NMR (400 MHz, CDCl₃) δ 8.95 (s, 1H), 8.29 (s, 1H), 8.18 (d, 1H, J = 7.90 Hz), 7.47 (d, 1H, J = 7.90 Hz), 7.32 (t, 1H, J = 7.77 Hz), 7.08 (d, 1H, J = 7.66 Hz), 6.96-7.01 (m, 2H), 4.79 (s, 2H), 4.33 (s, 2H), 3.60 (q, 2H, J = 5.55 Hz), 2.59 (t, 2H, J = 5.31 Hz), 2.51 (s, 4H), 1.83 (t, 2H, J = 5.33 Hz), 1.67-1.72 (m, 4H), 1.53 (s, 2H) |
| 3 | 2-(4-fluorobenzyl)-3-oxo-N-(3-(piperidin-1-yl)propyl)isoindoline-5-carboxamide HCl | ¹H NMR (400 MHz, CDCl₃) δ 8.98 (s, 1H), 8.26 (s, 1H), 8.15 (d, 1H, J = 7.90 Hz), 7.46 (d, 1H, J = 7.87 Hz), 7.28-7.30 (m, 2H), 7.00-7.04 (m, 2H), 4.77 (s, 2H), 4.29 (s, 2H), 3.59 (q, 2H, J = 5.66 Hz), 2.57 (t, 2H, J = 5.62 Hz), 2.49 (s, 4H), 1.79-1.84 (m, 2H), 1.65-1.70 (m, 4H), 1.51 (s, 2H) |
| 4 | 2-(3-chlorobenzyl)-3-oxo-N-(3-(piperidin-1-yl)propyl)isoindoline-5-carboxamide HCl | ¹H NMR (400 MHz, CDCl₃) δ 8.93 (s, 1H), 8.29 (s, 1H), 8.17 (d, 1H, J = 7.88 Hz), 7.47 (d, 1H, J = 7.92 Hz), 7.26-7.29 (m, 3H), 7.18-7.23 (m, 1H), 4.79 (s, 2H), 4.32 (s, 2H), 3.60 (q, 2H, J = 5.49 Hz), 2.56-2.59 (m, 2H), 2.51 (s, 2H), 1.82 (t, 2H, J = 5.63 Hz), 1.67-1.71 (m, 4H), 1.66 (s, 4H) |

TABLE 1-continued

| Cpd Nos | Compounds | $^1$H NMR |
|---|---|---|
| 5 | 2-(4-chlorobenzyl)-3-oxo-N-(3-(piperidin-1-yl)propyl)isoindoline-5-carboxamide HCl 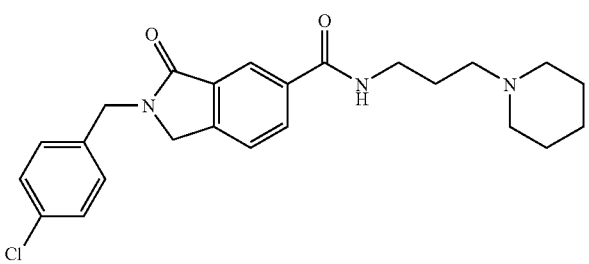 | $^1$H NMR (400 MHz, CDCl$_3$) δ 8.94 (s, 1H), 8.30 (s, 1H), 8.18 (d, 1H, J = 7.91 Hz), 7.47 (d, 1H, J = 7.85 Hz), 7.30-7.34 (m, 2H), 7.22-7.26 (m, 2H), 4.79 (s, 2H), 4.30 (s, 2H), 3.59-3.65 (m, 2H), 2.37-2.70 (m, 4H), 1.85 (s, 2H), 1.71 (s, 4H), 1.58 (s, 4H) |
| 6 | 2-(3-bromobenzyl)-3-oxo-N-(3-(piperidin-1-yl)propyl)isoindoline-5-carboxamide HCl 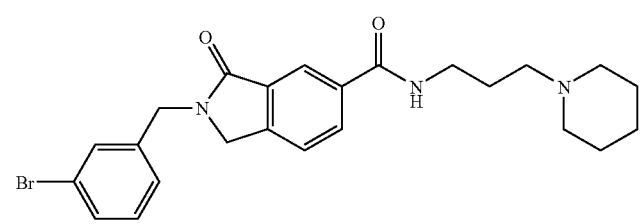 | $^1$H NMR (400 MHz, CDCl$_3$) δ 8.98 (s, 1H), 8.28 (s, 1H), 8.17 (d, 1H, J = 7.88 Hz), 7.42-7.49 (m, 3H), 7.21-7.24 (m, 2H), 4.78 (s, 2H), 4.32 (s, 2H), 3.58-3.62 (m, 2H), 2.55 (t, 2H, J = 5.56 Hz), 2.46 (s, 4H), 1.77-1.83 (m, 2H), 1.64-1.70 (m, 4H), 1.51 (s, 2H) |
| 7 | 2-(4-bromobenzyl)-3-oxo-N-(3-(piperidin-1-yl)propyl)isoindoline-5-carboxamide HCl 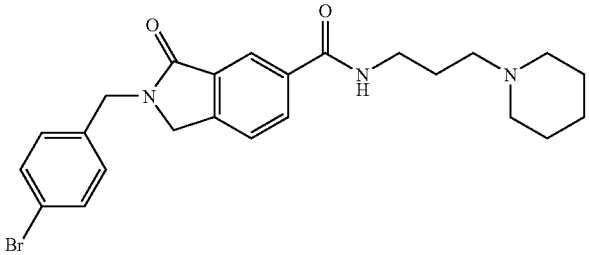 | $^1$H NMR (400 MHz, CDCl$_3$) δ 8.98 (s, 1H), 8.26 (s, 1H), 8.16 (d, 1H, J = 7.88 Hz), 7.46-7.49 (m, 3H), 7.20 (t, 2H, J = 7.32 Hz), 4.77 (s, 2H), 4.30 (s, 2H), 3.60 (q, 2H, J = 5.68 Hz), 2.54 (t, 2H, J = 5.58 Hz), 2.46 (s, 2H), 1.76-1.82 (m, 2H), 1.64-1.69 (m, 4H), 1.60 (s, 2H), 1.51 (s, 2H) |
| 8 | 2-(3-iodobenzyl)-3-oxo-N-(3-(piperidin-1-yl)propyl)isoindoline-5-carboxamide HCl 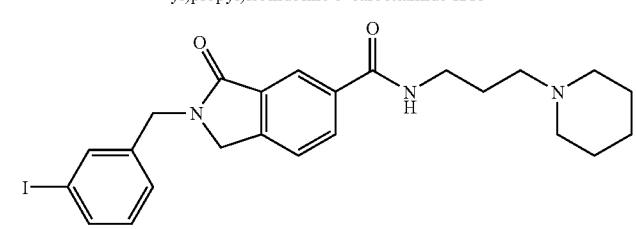 | $^1$H NMR (400 MHz, CDCl$_3$) δ 8.97 (s, 1H), 8.28 (s, 1H), 8.17 (d, 1H, J = 7.88 Hz), 7.66 (s, 1H), 7.63 (d, 1H, J = 7.92 Hz), 7.47 (d, 1H, J = 7.92 Hz), 7.28 (s, 1H), 7.08 (t, 1H, J = 7.72 Hz), 4.74 (s, 2H), 4.30 (s, 2H), 3.60 (q, 2H, J = 5.64 Hz), 2.56 (t, 2H, J = 5.52 Hz), 2.47 (s, 2H), 1.78-1.83 (m, 2H), 1.63-1.71 (m, 6H), 1.52 (s, 2H) |
| 9 | 2-(4-iodobenzyl)-3-oxo-N-(3-(piperidin-1-yl)propyl)isoindoline-5-carboxamide HCl 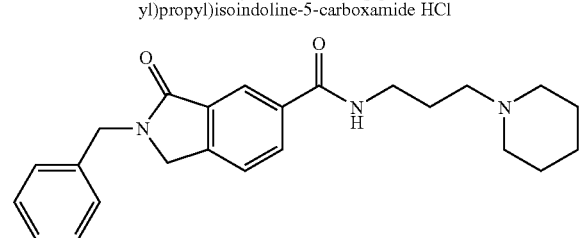 | $^1$H NMR (400 MHz, CDCl$_3$) δ 8.93 (s, 1H), 8.22 (s, 1H), 8.09 (d, 1H, J = 6.28 Hz), 7.60-7.63 (m, 2H), 7.40 (t, 1H, J = 7.56 Hz), 7.00 (d, 2H, J = 8.32 Hz), 4.70 (s, 2H), 4.25 (s, 2H), 3.54 (q, 2H, J = 5.64 Hz), 2.50 (t, 2H, J = 5.72 Hz), 2.42 (s, 4H), 1.73-1.79 (m, 2H), 1.59-1.66 (m, 4H), 1.46 (s, 2H) |

TABLE 1-continued

| Cpd Nos | Compounds | ¹H NMR |
|---|---|---|
| 10 | 2-benzyl-N-(3-(2-methylpiperidin-1-yl)propyl)-3-oxoisoindoline-5-carboxamide HCl | ¹H NMR (400 MHz, CDCl$_3$) δ 8.91 (s, 1H), 8.27 (s, 1H), 8.14 (d, 1H, J = 7.88 Hz), 7.44 (d, 1H, J = 7.92 Hz), 7.27-7.36 (m, 5H), 4.81 (s, 2H), 4.29 (s, 2H), 3.71-3.75 (m, 1H), 3.41-3.47 (m, 1H), 2.97-3.04 (m, 2H), 2.34-2.39 (m, 2H), 2.04-2.15 (m, 1H), 1.81-1.94 (m, 1H), 1.57-1.75 (m, 5H), 1.47-1.50 (m, 1H), 1.33-1.35 (m, 1H), 1.10 (d, 3H, J = 6.23 Hz) |
| 11 | 2-(3-fluorobenzyl)-N-(3-(2-methylpiperidin-1-yl)propyl)-3-oxoisoindoline-5-carboxamide HCl | ¹H NMR (400 MHz, CDCl$_3$) δ 8.98 (s, 1H), 8.27 (s, 1H), 8.16 (d, 1H, J = 7.90 Hz), 7.47 (d, 1H, J = 7.90 Hz), 7.31 (d, 1H, J = 7.74 Hz), 7.08 (d, 1H, J = 7.60 Hz), 6.99 (t, 2H, J = 8.75 Hz), 4.79 (s, 2H), 4.33 (s, 2H), 3.68-3.86 (m, 1H), 3.32-3.48 (m, 1H), 3.00-3.04 (m, 2H), 2.22-2.38 (m, 2H), 1.99-2.10 (m, 1H), 1.78-1.91 (m, 1H), 1.51-1.79 (m, 5H), 1.39-1.51 (m, 1H), 1.21-1.39 (m, 1H), 1.09 (d, 3H, J = 6.21 Hz) |
| 12 | 2-(4-fluorobenzyl)-N-(3-(2-methylpiperidin-1-yl)propyl)-3-oxoisoindoline-5-carboxamide HCl | ¹H NMR (400 MHz, CDCl$_3$) δ 8.93 (s, 1H), 8.26 (s, 1H), 8.15 (d, 1H, J = 7.91 Hz), 7.45 (t, 1H, J = 7.97 Hz), 7.26-7.30 (m, 2H), 7.00-7.04 (m, 2H), 4.78 (s, 2H), 4.29 (s, 2H), 3.68-3.80 (m, 1H), 3.32-3.47 (m, 1H), 2.88-3.06 (m, 2H), 2.22-2.37 (m, 2H), 1.98-2.10 (m, 1H), 1.76-1.89 (m, 1H), 1.52-1.77 (m, 5H), 1.38-1.51 (m, 1H), 1.22-1.38 (m, 1H), 1.09 (d, 3H, J = 6.23 Hz) |
| 13 | 2-(3-chlorobenzyl)-N-(3-(2-methylpiperidin-1-yl)propyl)-3-oxoisoindoline-5-carboxamide HCl | ¹H NMR (400 MHz, CDCl$_3$) δ 8.97 (s, 1H), 8.27 (s, 1H), 8.17 (d, 1H, J = 7.91 Hz), 7.47 (d, 1H, J = 7.99 Hz), 7.26-7.29 (m, 3H), 7.18-7.20 (m, 1H), 4.79 (s, 2H), 4.32 (s, 2H), 3.69-3.82 (m, 1H), 3.32-3.49 (m, 1H), 2.97-3.05 (m, 2H), 2.23-2.40 (m, 2H), 2.00-2.12 (m, 1H), 1.79-1.93 (m, 1H), 1.52-1.79 (m, 5H), 1.38-1.52 (m, 1H), 1.27-1.38 (m, 1H), 1.10 (d, 3H, J = 6.23 Hz) |
| 14 | 2-(4-chlorobenzyl)-N-(3-(2-methylpiperidin-1-yl)propyl)-3-oxoisoindoline-5-carboxamide HCl | ¹H NMR (400 MHz, CDCl$_3$) δ 8.94 (s, 1H), 8.28 (s, 1H), 8.17 (d, 1H, J = 7.89 Hz), 7.47 (d, 1H, J = 7.88 Hz), 7.30-7.33 (m, 2H), 7.24-7.26 (m, 2H), 4.78 (s, 2H), 4.30 (s, 2H), 3.68-3.82 (m, 1H), 3.40-3.51 (m, 1H), 2.93-3.11 (m, 2H), 2.27-2.44 (m, 2H), 1.98-2.18 (m, 1H), 1.79-1.98 (m, 1H), 1.53-1.79 (m, 5H), 1.34-1.52 (m, 1H), 1.29-1.34 (m, 1H), 1.11 (d, 3H, J = 6.07 Hz) |

TABLE 1-continued

| Cpd Nos | Compounds | $^1$H NMR |
|---|---|---|
| 15 | 2-(3-bromobenzyl)-N-(3-(2-methylpiperidin-1-yl)propyl)-3-oxoisoindoline-5-carboxamide HCl | $^1$H NMR (400 MHz, CDCl$_3$) δ 8.98 (s, 1H), 8.27 (s, 1H), 8.17 (d, 1H, J = 7.89 Hz), 7.41-7.52 (m, 3H), 7.19-7.25 (m, 2H), 4.78 (s, 2H), 4.32 (s, 2H), 3.73-3.77 (m, 1H), 3.40-3.46 (m, 1H), 2.97-3.03 (m, 2H), 2.31-2.36 (m, 2H), 2.00-2.11 (m, 1H), 1.82-1.94 (m, 1H), 1.53-1.79 (m, 5H), 1.39-1.53 (m, 1H), 1.28-1.39 (m, 1H), 1.09 (d, 3H, J = 6.18 Hz) |
| 16 | 2-(4-bromobenzyl)-N-(3-(2-methylpiperidin-1-yl)propyl)-3-oxoisoindoline-5-carboxamide HCl | $^1$H NMR (400 MHz, CDCl$_3$) δ 8.97 (s, 1H), 8.26 (s, 1H), 8.16 (d, 1H, J = 7.85 Hz), 7.46 (d, 3H, J = 8.09 Hz), 7.18 (d, 2H, J = 8.25 Hz), 4.74 (s, 2H), 4.30 (s, 2H), 3.73-3.78 (m, 1H), 3.42-3.46 (m, 1H), 2.97-3.04 (m, 2H), 2.30-2.36 (m, 2H), 1.99-2.10 (m, 1H), 1.78-1.93 (m, 1H), 1.52-1.78 (m, 5H), 1.41-1.52 (m, 1H), 1.28-1.41 (m, 1H), 1.09 (d, 3H, J = 6.19 Hz) |
| 17 | 2-(3-iodobenzyl)-N-(3-(2-methylpiperidin-1-yl)propyl)-3-oxoisoindoline-5-carboxamide HCl | $^1$H NMR (400 MHz, CDCl$_3$) δ 8.91 (s, 1H), 8.28 (s, 1H), 8.15 (d, 1H, J = 7.90 Hz), 7.65 (s, 1H), 7.61 (d, 1H, J = 8.24 Hz), 7.46 (d, 1H, J = 7.90 Hz), 7.25-7.27 (m, 1H), 7.01-7.08 (m, 1H), 4.74 (s, 2H), 4.29 (s, 2H), 3.68-3.74 (m, 1H), 3.42-3.48 (m, 1H), 3.00-3.05 (m, 2H), 2.37-2.41 (m, 2H), 2.08-2.19 (m, 1H), 1.98-2.04 (m, 1H), 1.84-1.94 (m, 1H), 1.57-1.81 (m, 4H), 1.43-1.57 (m, 1H), 1.31-1.42 (m, 1H), 1.12 (d, 3H, J = 6.19 Hz) |
| 18 | 2-(4-iodobenzyl)-N-(3-(2-methylpiperidin-1-yl)propyl)-3-oxoisoindoline-5-carboxamide HCl | $^1$H NMR (400 MHz, CDCl$_3$) δ 8.90 (s, 1H), 8.25 (s, 1H), 8.12 (d, 1H, J = 7.91 Hz), 7.62 (d, 2H, J = 8.16 Hz), 7.41 (d, 2H, J = 7.91 Hz), 7.01 (d, 2H, J = 8.15 Hz), 4.66 (s, 2H), 4.27 (s, 2H), 3.65-3.69 (m, 1H), 3.41-3.45 (m, 1H), 3.00-3.04 (m, 2H), 2.36-2.48 (m, 2H), 2.11-2.21 (m, 1H), 1.84-2.03 (m, 1H), 1.58-1.82 (m, 5H), 1.44-1.58 (m, 1H), 1.28-1.39 (m, 1H), 1.10 (d, 3H, J = 6.23 Hz) |
| 19 | 2-benzyl-N-(3-(2-ethylpiperidin-1-yl)propyl)-3-oxoisoindoline-5-carboxamide HCl | $^1$H NMR (400 MHz, CDCl$_3$) δ 8.78 (s, 1H), 8.21 (s, 1H), 8.08 (d, 1H, J = 7.82 Hz), 7.40 (d, 1H, J = 7.84 Hz), 7.20-7.32 (m, 5H), 4.70 (s, 2H), 4.26 (s, 2H), 3.69-3.71 (m, 1H), 3.55-3.60 (m, 2H), 2.91-2.98 (m, 2H), 2.42-2.45 (m, 1H), 2.18-2.30 (m, 2H), 1.96-2.03 (m, 1H), 1.72-1.90 (m, 2H), 1.52-1.72 (m, 3H), 1.38-1.52 (m, 2H), 1.26-1.38 (m, 1H), 0.84 (t, 3H, J = 7.31 Hz) |

TABLE 1-continued

| Cpd Nos | Compounds | ¹H NMR |
|---|---|---|
| 20 | N-(3-(2-ethylpiperidin-1-yl)propyl)-2-(3-fluorobenzyl)-3-oxoisoindoline-5-carboxamide HCl | ¹H NMR (400 MHz, CDCl₃) δ 8.99 (s, 1H), 8.26 (s, 1H), 8.16 (d, 1H, J = 7.89 Hz), 7.47 (d, 1H, J = 7.86 Hz), 7.30 (q, 1H, J = 5.93 Hz), 7.07 (d, 1H, J = 7.66 Hz), 6.98-7.01 (m, 2H), 4.80 (s, 2H), 4.32 (s, 2H), 3.69-3.81 (m, 1H), 3.39-3.48 (m, 1H), 2.93-3.08 (m, 2H), 2.29-2.41 (m, 1H), 2.03-2.20 (m, 2H), 1.79-1.92 (m, 1H), 1.63-1.79 (m, 3H), 1.39-1.63 (m, 5H), 1.20-1.48 (m, 1H), 0.88 (t, 3H, J = 7.45 Hz) |
| 21 | N-(3-(2-ethylpiperidin-1-yl)propyl)-2-(4-fluorobenzyl)-3-oxoisoindoline-5-carboxamide HCl | ¹H NMR (400 MHz, CDCl₃) δ 8.95 (s, 1H), 8.27 (s, 1H), 8.16 (d, 1H, J = 7.90 Hz), 7.46 (d, 1H, J = 7.88 Hz), 7.27-7.31 (m, 2H), 7.01-7.05 (m, 2H), 4.79 (s, 2H), 4.30 (s, 2H), 3.72-3.75 (m, 1H), 3.47-3.50 (m, 1H), 2.92-3.10 (m, 2H), 2.30-2.47 (m, 1H), 2.06-2.30 (m, 2H), 1.82-1.97 (m, 1H), 1.69-1.82 (m, 3H), 1.42-1.68 (m, 5H), 1.29-1.42 (m, 1H), 0.89 (t, 3H, J = 7.44 Hz) |
| 22 | 2-(3-chlorobenzyl)-N-(3-(2-ethylpiperidin-1-yl)propyl)-3-oxoisoindoline-5-carboxamide HCl | ¹H NMR (400 MHz, CDCl₃) δ 8.97 (s, 1H), 8.27 (s, 1H), 8.17 (d, 1H, J = 7.91 Hz), 7.47 (d, 1H, J = 7.94 Hz), 7.26-7.29 (m, 3H), 7.18-7.20 (m, 1H), 4.79 (s, 2H), 4.32 (s, 2H), 3.67-3.81 (m, 1H), 3.37-3.48 (m, 1H), 2.93-3.09 (m, 2H), 2.30-2.43 (m, 1H), 2.08-2.22 (m, 2H), 1.81-1.94 (m, 1H), 1.67-1.81 (m, 3H), 1.42-1.67 (m, 5H), 1.28-1.42 (m, 1H), 0.88 (t, 3H, J = 7.44 Hz) |
| 23 | 2-(4-chlorobenzyl)-N-(3-(2-ethylpiperidin-1-yl)propyl)-3-oxoisoindoline-5-carboxamide HCl | ¹H NMR (400 MHz, CDCl₃) δ 8.99 (s, 1H), 8.26 (s, 1H), 8.16 (d, 1H, J = 7.89 Hz), 7.45 (d, 1H, J = 7.91 Hz), 7.30-7.33 (m, 2H), 7.24-7.27 (m, 2H), 4.78 (s, 2H), 4.30 (s, 2H), 3.64-3.80 (m, 1H), 3.35-3.49 (m, 1H), 2.92-3.08 (m, 2H), 2.28-2.40 (m, 1H), 2.03-2.21 (m, 2H), 1.78-1.92 (m, 1H), 1.63-1.88 (m, 3H), 1.41-1.63 (m, 5H), 1.27-1.41 (m, 1H), 0.88 (t, 3H, J = 7.45 Hz) |

TABLE 1-continued

| Cpd Nos | Compounds | $^1$H NMR |
|---|---|---|
| 24 | 2-(3-bromobenzyl)-N-(3-(2-methylpiperidin-1-yl)propyl)-3-oxoisoindoline-5-carboxamide HCl | $^1$H NMR (400 MHz, CDCl$_3$) δ 9.01 (s, 1H), 8.25 (s, 1H), 8.17 (d, 1H, J = 7.90 Hz), 7.40-7.49 (m, 3H), 7.19-7.25 (m, 2H), 4.78 (s, 2H), 4.32 (s, 2H), 3.73-3.77 (m, 1H), 3.43-3.48 (m, 1H), 3.00-3.05 (m, 2H), 2.35-2.38 (m, 1H), 2.12-2.24 (m, 2H), 1.83-1.94 (m, 1H), 1.44-1.78 (m, 8H), 1.28-1.40 (m, 1H), 0.88 (t, 3H, J = 7.45 Hz) |
| 25 | 2-(4-bromobenzyl)-N-(3-(2-methylpiperidin-1-yl)propyl)-3-oxoisoindoline-5-carboxamide HCl | $^1$H NMR (400 MHz, CDCl$_3$) δ 9.00 (s, 1H0, 8.25 (s, 1H), 8.16 (d, 1H, J = 7.91 Hz), 7.46 (d, 3H, J = 8.32 Hz), 7.18 (d, 2H, J = 8.27 Hz), 4.77 (s, 2H), 4.30 (s, 2H), 3.72-3.76 (m, 1H), 3.44-3.50 (m, 1H), 2.98-3.05 (m, 2H), 2.35-2.38 (m, 1H), 2.12-2.22 (m, 2H), 1.82-1.93 (m, 1H), 1.43-1.77 (m, 8H), 1.28-1.49 (m, 1H), 0.88 (t, 3H, J = 7.40 Hz) |
| 26 | N-(3-(2-ethylpiperidin-1-yl)propyl)-2-(3-iodobenzyl)-3-oxoisoindoline-5-carboxamide HCl | $^1$H NMR (400 MHz, CDCl$_3$) δ 9.00 (s, 1H), 8.26 (s, 1H), 8.17 (d, 1H, J = 7.89 Hz), 7.66 (s, 1H), 7.63 (d, 1H, J = 7.94 Hz), 7.47 (d, 1H, J = 7.90 Hz), 7.29 (s, 1H), 7.08 (t, 1H, J = 7.74 Hz), 4.76 (s, 2H), 4.31 (s, 2H), 3.72-3.77 (m, 1H), 3.43-3.49 (m, 1H), 2.98-3.05 (m, 2H), 2.35-2.39 (m, 1H), 1.82-1.94 (m, 1H), 1.45-1.78 (m, 10H), 1.39-1.41 (m, 1H), 0.88 (t, 3H, J = 7.45 Hz) |
| 27 | N-(3-(2-ethylpiperidin-1-yl)propyl)-2-(4-iodobenzyl)-3-oxoisoindoline-5-carboxamide HCl | $^1$H NMR (400 MHz, CDCl$_3$) δ 8.95 (s, 1H), 8.22 (s, 1H), 8.10 (d, 1H, J = 7.91 Hz), 7.60 (d, 2H, J = 8.33 Hz), 7.42 (d, 1H, J = 7.86 Hz), 7.01 (d, 2H, J = 8.32 Hz), 4.70 (s, 2H), 4.25 (s, 2H), 3.65-2.69 (m, 1H), 3.40-3.45 (m, 1H), 2.93-3.00 (m, 2H), 2.27-2.41 (m, 1H), 2.06-2.19 (m, 2H), 1.78-1.91 (m, 1H), 1.40-1.76 (m, 8H), 1.24-1.37 (m, 1H), 0.84 (t, 3H, J = 7.44 Hz) |

TABLE 1-continued

| Cpd Nos | Compounds | ¹H NMR |
|---|---|---|
| 28 | 2-benzyl-3-oxo-N-(3-(2-propylpiperidin-1-yl)propyl)isoindoline-5-carboxamide HCl | ¹H NMR (400 MHz, CDCl₃) δ 8.87 (s, 1H), 8.29 (s, 1H), 8.14 (d, 1H, J = 7.88 Hz), 7.42 (d, 1H, J = 7.88 Hz), 7.26-7.35 (m, 5H), 4.80 (s, 2H), 4.28 (s, 2H), 3.65-3.70 (m, 1H), 3.46-3.52 (m, 2H), 3.00-3.05 (m, 2H), 2.40-2.58 (m, 2H), 1.84-1.96 (m, 1H), 1.67-1.84 (m, 3H), 1.50-1.67 (m, 4H), 1.29-1.50 (m, 3H), 1.16-1.29 (m, 2H), 0.85 (t, 3H, J = 7.26 Hz) |
| 29 | 2-(3-fluorobenzyl)-3-oxo-N-(3-(2-propylpiperidin-1-yl)propyl)isoindoline-5-carboxamide HCl | ¹H NMR (400 MHz, CDCl₃) δ 9.04 (s, 1H), 8.25 (s, 1H), 8.16 (d, 1H, J = 7.89 Hz), 7.46 (d, 1H, J = 7.90 Hz), 7.28 (q, 1H, J = 5.89 Hz), 7.07 (d, 1H, J = 7.52 Hz), 7.00 (d, 2H, J = 8.70 Hz), 4.80 (s, 2H), 4.32 (s, 2H), 3.69-3.74 (m, 1H), 3.44-3.48 (m, 1H), 2.96-3.02 (m, 2H), 2.32-2.43 (m, 1H), 2.11-2.28 (m, 2H), 1.78-1.93 (m, 1H), 1.67-1.76 (m, 3H), 1.46-1.67 (m, 4H), 1.18-1.46 (m, 4H), 0.86 (t, 3H, J = 7.27 Hz) |
| 30 | 2-(4-fluorobenzyl)-3-oxo-N-(3-(2-propylpiperidin-1-yl)propyl)isoindoline-5-carboxamide HCl | ¹H NMR (400 MHz, CDCl₃) δ 8.97 (s, 1H), 8.23 (s, 1H), 8.13 (d, 1H, J = 7.90 Hz), 7.45 (d, 1H, J = 7.91 Hz), 7.25-7.29 (m, 2H), 7.00-7.04 (m, 2H), 4.77 (s, 2H), 4.29 (s, 2H), 3.62-3.66 (m, 1H), 3.42-3.50 (m, 1H), 2.93-2.98 (m, 2H), 2.35-2.38 (m, 1H), 2.15-2.24 (m, 2H), 1.77-1.89 (m, 2H), 1.46-1.77 (m, 6H), 1.18-1.46 (m, 4H), 0.86 (t, 3H, J = 7.22 Hz) |
| 31 | 2-(3-chlorobenzyl)-3-oxo-N-(3-(2-propylpiperidin-1-yl)propyl)isoindoline-5-carboxamide HCl | ¹H NMR (400 MHz, CDCl₃) δ 9.03 (s, 1H), 8.24 (s, 1H), 8.15 (d, 1H, J = 7.89 Hz), 7.46 (d, 1H, J = 7.88 Hz), 7.25-7.28 (m, 3H), 7.17-7.19 (m, 1H), 4.77 (s, 2H), 4.31 (s, 2H), 3.68-3.74 (m, 1H), 3.45-3.49 (m, 1H), 2.95-3.01 (m, 2H), 2.33-2.41 (m, 1H), 2.21-2.27 (m, 1H), 2.10-2.18 (m, 2H), 1.78-1.90 (m, 1H), 1.66-1.76 (m, 3H), 1.46-1.63 (m, 3H), 1.28-1.46 (m, 3H), 1.18-1.29 (m, 1H), 0.86 (t, 3H, J = 7.24 Hz) |

TABLE 1-continued

| Cpd Nos | Compounds | ¹H NMR |
|---|---|---|
| 32 | 2-(4-chlorobenzyl)-3-oxo-N-(3-(2-propylpiperidin-1-yl)propyl)isoindoline-5-carboxamide HCl | ¹H NMR (400 MHz, CDCl$_3$) δ 9.03 (s, 1H), 8.24 (s, 1H), 8.16 (d, 1H, J = 7.88 Hz), 7.46 (d, 1H, J = 7.87 Hz), 7.45-7.48 (m, 2H), 7.23-7.25 (m, 2H), 4.78 (s, 2H), 4.30 (s, 2H), 3.70-3.74 (m, 1H), 3.44-3.50 (m, 1H), 2.96-3.03 (m, 2H), 2.36-2.40 (m, 1H), 2.11-2.19 (m, 2H), 1.78-1.92 (m, 1H), 1.46-1.78 (m, 7H), 1.28-1.46 (m, 3H), 1.19-1.28 (m, 1H), 0.87 (t, 3H, J = 7.22 Hz) |
| 33 | 2-(3-bromobenzyl)-3-oxo-N-(3-(2-propylpiperidin-1-yl)propyl)isoindoline-5-carboxamide HCl | ¹H NMR (400 MHz, CDCl$_3$) δ 9.02 (s, 1H), 8.25 (s, 1H), 8.16 (d, 1H, J = 7.89 Hz), 7.52 (s, 1H), 7.40-7.49 (m, 2H), 7.19-7.25 (m, 2H), 4.78 (s, 2H), 4.32 (s, 2H), 3.70-3.74 (m, 1H), 3.47-3.50 (m, 1H), 2.97-3.03 (m, 2H), 2.36-2.40 (m, 1H), 2.12-2.28 (m, 2H), 1.80-1.93 (m, 1H), 1.47-1.77 (m, 7H), 1.19-1.47 (m, 4H), 0.87 (t, 3H, J = 7.24 Hz) |
| 34 | 2-(4-bromobenzyl)-3-oxo-N-(3-(2-propylpiperidin-1-yl)propyl)isoindoline-5-carboxamide HCl | ¹H NMR (400 MHz, CDCl$_3$) δ 9.00 (s, 1H), 8.25 (s, 1H), 8.16 (d, 1H, J = 7.88 Hz), 7.45-7.52 (m, 3H), 7.18 (d, 2H, J = 8.39 Hz), 4.76 (s, 2H), 4.30 (s, 2H), 3.69-3.75 (m, 1H), 3.44-3.50 (m, 1H), 2.98-3.03 (m, 2H), 2.37-2.41 (m, 1H), 2.13-2.32 (m, 2H), 1.79-1.93 (m, 1H), 1.47-1.79 (m, 7H), 1.19-1.47 (m, 4H), 0.87 (t, 3H, J = 7.22 Hz) |
| 35 | 2-(3-iodobenzyl)-3-oxo-N-(3-(2-propylpiperidin-1-yl)propyl)isoindoline-5-carboxamide HCl | ¹H NMR (400 MHz, CDCl$_3$) δ 8.98 (s, 1H), 8.27 (s, 1H), 8.17 (d, 1H, J = 7.90 Hz), 7.66 (s, 1H), 7.63 (d, 1H, J = 7.93 Hz), 7.47 (d, 1H, J = 7.92 Hz), 7.29 (s, 1H), 7.08 (t, 1H, J = 7.75 Hz), 4.74 (s, 2H), 4.32 (s, 2H), 3.67-3.76 (m, 1H), 3.46-3.52 (m, 1H), 2.96-3.08 (m, 2H), 2.86-2.97 (m, 1H), 2.15-2.33 (m, 2H), 1.81-1.93 (m, 1H), 1.49-1.81 (m, 7H), 1.19-1.48 (m, 4H), 0.87 (t, 3H, J = 7.22 Hz) |

TABLE 1-continued

| Cpd Nos | Compounds | ¹H NMR |
|---|---|---|
| 36 | 2-(4-iodobenzyl)-3-oxo-N-(3-(2-propylpiperidin-1-yl)propyl)isoindoline-5-carboxamide HCl | ¹H NMR (400 MHz, CDCl$_3$) δ 8.99 (s, 1H), 8.26 (s, 1H), 8.16 (d, 1H, J = 7.87 Hz), 7.67 (d, 2H, J = 8.29 Hz), 7.46 (d, 1H, J = 7.93 Hz), 7.05 (d, 2H, J = 8.25 Hz), 4.74 (s, 2H), 4.29 (s, 2H), 3.68-3.75 (m, 1H), 3.45-3.51 (m, 1H), 2.96-3.07 (m, 2H), 2.34-2.47 (m, 1H), 2.13-2.30 (m, 2H), 1.79-1.93 (m, 1H), 1.50-1.79 (m, 7H), 1.22-1.47 (m, 4H), 0.87 (t, 3H, J = 7.25 Hz) |
| 37 | 2-benzyl-3-oxo-N-(3-(2-propylpiperidin-1-yl)propyl)isoindoline-5-carboxamide HCl | ¹H NMR (400 MHz, CDCl$_3$) δ 8.71 (s, 1H), 8.25 (s, 1H), 8.13 (d, 1H, J = 9.33 Hz), 7.42 (d, 1H, J = 7.91 Hz), 7.25-7.39 (m, 5H), 4.80 (s, 2H), 4.28 (s, 2H), 3.74-3.80 (m, 1H), 3.40-3.42 (m, 1H), 3.20 (d, 1H, J = 11.73 Hz), 3.08-3.13 (m, 1H), 2.28-2.39 (m, 1H), 2.13-2.24 (m, 1H), 1.84-2.11 (m, 3H), 1.62-1.84 (m, 3H), 1.38-1.58 (m, 3H), 1.22-1.27 (m, 1H), 0.89 (q, 6H, J = 5.22 Hz) |
| 38 | 2-(3-fluorobenzyl)-N-(3-(2-isopropylpiperidin-1-yl)propyl)-3-oxoisoindoline-5-carboxamide HCl | ¹H NMR (400 MHz, CDCl$_3$) δ 8.76 (s, 1H), 8.23 (s, 1H), 8.13 (d, 1H, J = 8.13 Hz), 7.44 (d, 1H, J = 7.91 Hz), 7.26-7.31 (m, 1H), 7.05 (d, 1H, J = 7.58 Hz), 6.91-7.01 (m, 2H), 4.78 (s, 2H), 4.73 (s, 2H), 3.75-3.80 (m, 1H), 3.37-3.40 (m, 1H), 3.17 (d, 1H, J = 11.81 Hz), 3.04-3.09 (m, 1H), 2.23-2.32 (m, 1H), 2.13-2.23 (m, 1H), 1.83-2.04 (m, 3H), 1.74-1.83 (m, 1H), 1.58-1.74 (m, 2H), 1.47-1.27 (m, 1H), 0.89 (q, 6H, J = 5.22 Hz) |
| 39 | 2-(4-fluorobenzyl)-N-(3-(2-isopropylpiperidin-1-yl)propyl)-3-oxoisoindoline-5-carboxamide HCl | ¹H NMR (400 MHz, CDCl$_3$) δ 8.72 (s, 1H), 8.23 (s, 1H), 8.11 (d, 1H, J = 7.91 Hz), 7.41 (d, 1H, J = 7.88 Hz), 7.23-7.30 (m, 2H), 6.94-7.02 (m, 2H), 4.74 (s, 2H), 4.26 (s, 2H), 3.71-3.76 (m, 1H), 3.37-3.42 (m, 1H), 3.18 (d, 1H, J = 11.89 Hz), 3.07-3.09 (m, 1H), 2.29-2.41 (m, 1H), 2.12-2.24 (m, 1H), 1.85-2.12 (m, 3H), 1.67-1.82 (m, 1H), 1.59-1.67 (m, 1H), 1.38-1.59 (m, 3H), 1.17-1.32 (m, 1H), 0.87 (q, 6H, J = 5.38 Hz) |

TABLE 1-continued

| Cpd Nos | Compounds | ¹H NMR |
|---|---|---|
| 40 | 2-(3-chlorobenzyl)-N-(3-(2-isopropylpiperidin-1-yl)propyl)-3-oxoisoindoline-5-carboxamide HCl | ¹H NMR (400 MHz, CDCl$_3$) δ 8.75 (s, 1H), 8.27 (s, 1H), 8.16 (d, 1H, J = 7.89 Hz), 7.45 (d, 1H, J = 7.93 Hz), 7.23-7.29 (m, 3H), 7.14-7.19 (m, 1H), 4.77 (s, 2H), 4.30 (s, 2H), 3.73-3.78 (m, 1H), 3.41-3.46 (m, 1H), 3.25 (d, 1H, J = 11.85 Hz), 3.14-3.18 (m, 1H), 2.38-2.51 (m, 1H), 2.06-2.24 (m, 3H), 1.92-2.06 (m, 1H), 1.74-1.88 (m, 2H), 1.64-1.73 (m, 1H), 1.46-1.63 (m, 3H), 1.24-1.32 (m, 1H), 0.89 (q, 6H, J = 6.77 Hz) |
| 41 | 2-(4-chlorobenzyl)-N-(3-(2-isopropylpiperidin-1-yl)propyl)-3-oxoisoindoline-5-carboxamide HCl | ¹H NMR (400 MHz, CDCl$_3$) δ 8.75 (s, 1H), 8.24 (s, 1H), 8.14 (d, 1H, J = 7.89 Hz), 7.44 (d, 1H, J = 7.87 Hz), 7.28-7.33 (m, 2H), 7.21-7.23 (m, 2H), 4.74 (s, 2H), 4.28 (s, 2H), 3.74-3.79 (m, 1H), 3.37-3.41 (m, 1H), 3.22 (d, 1H, J = 11.87 Hz), 3.10-3.14 (m, 1H), 2.29-2.43 (m, 1H), 2.15-2.24 (m, 1H), 1.87-2.14 (m, 3H), 1.62-1.84 (m, 3H), 1.42-1.62 (m, 3H), 1.24-1.26 (m, 1H), 0.90 (q, 6H, J = 5.31 Hz) |
| 42 | 2-(3-bromobenzyl)-N-(3-(2-isopropylpiperidin-1-yl)propyl)-3-oxoisoindoline-5-carboxamide HCl | ¹H NMR (400 MHz, CDCl$_3$) δ 8.77 (s, 1H), 8.24 (s, 1H), 8.13 (d, 1H, J = 7.90 Hz), 7.36-7.47 (m, 3H), 7.16-7.21 (m, 2H), 4.74 (s, 2H), 4.28 (s, 2H), 3.71-3.77 (m, 1H), 3.38-3.42 (m, 1H), 3.20 (d, 1H, J = 11.74 Hz), 3.08-3.13 (m, 1H), 2.31-2.44 (m, 1H), 1.87-2.24 (m, 4H), 1.61-1.84 (m, 3H), 1.37-1.61 (m, 3H), 1.22-1.27 (m, 1H), 0.85-0.89 (m, 6H) |
| 43 | 2-(4-bromobenzyl)-N-(3-(2-isopropylpiperidin-1-yl)propyl)-3-oxoisoindoline-5-carboxamide HCl | ¹H NMR (400 MHz, CDCl$_3$) δ 8.75 (s, 1H), 8.24 (s, 1H), 8.13 (d, 1H, J = 7.90 Hz), 7.44 (d, 3H, J = 8.33 Hz), 7.16 (d, 2H, J = 8.30 Hz), 4.74 (s, 2H), 4.28 (s, 2H), 3.70-3.82 (m, 1H), 3.33-3.44 (m, 1H), 3.20 (d, 1H, J = 11.56 Hz), 3.05-3.14 (m, 1H), 2.28-2.40 (m, 1H), 2.13-2.28 (m, 1H), 1.86-2.10 (m, 3H), 1.61-1.86 (m, 3H), 1.47-1.60 (m, 3H), 1.24-1.29 (m, 1H), 0.89 (t, 6H, J = 6.63 Hz) |

TABLE 1-continued

| Cpd Nos | Compounds | $^1$H NMR |
|---|---|---|
| 44 | 2-(3-iodobenzyl)-N-(3-(2-isopropylpiperidin-1-yl)propyl)-3-oxoisoindoline-5-carboxamide HCl | 1H NMR (400 MHz, CDCl$_3$) δ 8.78 (s, 1H), 8.26 (s, 1H), 8.13 (d, 1H, J = 7.88 Hz), 7.61 (s, 1H), 7.57 (d, 1H, J = 7.98 Hz), 7.40 (d, 1H, J = 7.91 Hz), 7.21 (d, 1H, J = 7.68 Hz), 7.03 (t, 1H, J = 7.75 Hz), 4.69 (s, 2H), 4.26 (s, 2H), 3.66-3.71 (m, 1H), 3.41-3.46 (m, 1H), 3.27 (d, 1H, J = 11.57 Hz), 3.12-3.17 (m, 1H), 2.58 (bs, 1H), 2.15-2.27 (m, 2H), 1.92-2.07 (m, 1H), 1.74-1.88 (m, 2H), 1.43-1.74 (m, 5H), 1.25-1.32 (m, 1H), 0.82-0.91 (m, 6H) |
| 45 | 2-(4-iodobenzyl)-N-(3-(2-isopropylpiperidin-1-yl)propyl)-3-oxoisoindoline-5-carboxamide HCl | $^1$H NMR (400 MHz, CDCl$_3$) δ 8.75 (s, 1H), 8.23 (s, 1H), 8.11 (d, 1H, J = 7.89 Hz), 7.62 (d, 2H, J = 8.28 Hz), 7.42 (d, 1H, J = 7.92 Hz), 7.02 (d, 2H, J = 8.26 Hz), 4.71 (s, 2H), 4.26 (s, 2H), 3.71-3.76 (m, 1H), 3.38-3.41 (m, 1H), 3.19 (d, 1H, J = 11.82 Hz), 3.07-3.12 (m, 1H), 2.28-2.43 (m, 1H), 2.12-2.25 (m, 1H), 1.86-2.12 (m, 3H), 1.58-1.86 (m, 3H), 1.36-1.58 (m, 3H), 1.22-1.27 (m, 1H), 0.86-0.89 (m, 6H) |
| 46 | 2-benzyl-N-(3-(2-butylpiperidin-1-yl)propyl)-3-oxoisoindoline-5-carboxamide HCl | $^1$H NMR (400 MHz, CDCl$_3$) δ 8.87 (s, 1H), 8.27 (s, 1H), 8.13 (d, 1H, J = 7.90 Hz), 7.42 (d, 1H, J = 7.90 Hz), 7.25-7.34 (m, 5H), 4.79 (s, 2H), 4.27 (s, 2H), 3.64-3.69 (m, 1H), 3.47-3.52 (m, 1H), 3.00-3.03 (m, 2H), 2.25-2.55 (m, 3H), 1.84-1.98 (m, 1H), 2.12-2.25 (m, 1H), 1.86-2.12 (m, 3H), 1.58-1.86 (m, 3H), 1.36-1.58 (m, 3H), 1.14-1.84 (m, 13H), 0.82 (t, 3H, J = 6.77 Hz) |
| 47 | N-(3-(2-butylpiperidin-1-yl)propyl)-2-(3-fluorobenzyl)-3-oxoisoindoline-5-carboxamide HCl | $^1$H NMR (400 MHz, CDCl$_3$) δ 8.94 (s, 1H), 8.26 (s, 1H), 8.15 (d, 1H, J = 7.69 Hz), 7.45 (d, 1H, J = 7.96 Hz), 7.23-7.32 (m, 1H), 7.06 (d, 1H, J = 7.76), 6.98 (d, 1H, J = 8.90 Hz), 4.79 (s, 2H), 4.31 (s, 2H), 3.66-3.70 (m, 1H), 3.48-3.51 (m, 1H), 2.97-3.03 (m, 2H), 2.19-2.44 (m, 3H), 1.81-1.95 (m, 1H), 1.16-1.81 (m, 13H), 0.82 (t, 3H, J = 6.85 Hz) |

TABLE 1-continued

| Cpd Nos | Compounds | ¹H NMR |
|---|---|---|
| 48 | N-(3-(2-butylpiperidin-1-yl)propyl)-2-(4-fluorobenzyl)-3-oxoisoindoline-5-carboxamide HCl | ¹H NMR (400 MHz, CDCl₃) δ 8.89 (s, 1H), 8.27 (s, 1H), 8.13 (d, 1H, J = 7.88 Hz), 7.44 (d, 1H, J = 7.89 Hz), 7.25-7.28 (m, 2H), 6.96-7.04 (m, 1H), 4.77 (s, 2H), 4.28 (s, 2H), 3.65-3.70 (m, 1H), 3.46-3.51 (m, 1H), 2.98-3.02 (m, 2H), 2.12-2.51 (m, 3H), 1.82-1.95 (m, 1H), 1.14-1.82 (m, 13H), 0.82 (t, 3H, J = 6.83 Hz) |
| 49 | N-(3-(2-butylpiperidin-1-yl)propyl)-2-(3-chlorobenzyl)-3-oxoisoindoline-5-carboxamide HCl | ¹H NMR (400 MHz, CDCl₃) δ 8.96 (s, 1H), 8.25 (s, 1H), 8.15 (d, 1H, J = 7.92 Hz), 7.46 (d, 1H, J = 7.90 Hz), 7.26-7.31 (m, 3H), 7.17-7.20 (m, 1H), 4.78 (s, 2H), 4.31 (s, 2H), 3.62-3.79 (m, 1H), 3.37-3.54 (m, 1H), 2.89-3.07 (m, 2H), 2.11-2.47 (m, 3H), 1.89-2.10 (m, 1H), 1.08-1.78 (m, 13H), 0.83 (t, 3H, J = 6.94 Hz) |
| 50 | N-(3-(2-butylpiperidin-1-yl)propyl)-2-(4-chlorobenzyl)-3-oxoisoindoline-5-carboxamide HCl | ¹H NMR (400 MHz, CDCl₃) δ 8.93 (s, 1H), 8.24 (s, 1H), 8.15 (d, 1H, J = 7.87 Hz), 7.43 (d, 1H, J = 7.87 Hz), 7.21-7.34 (m, 4H), 4.75 (s, 2H), 4.27 (s, 2H), 3.65-3.69 (m, 1H), 3.45-3.49 (m, 1H), 2.94-2.99 (m, 2H), 2.37-2.40 (m, 1H), 2.18-2.37 (m, 2H), 1.77-1.92 (m, 1H), 1.13-1.76 (m, 13H), 0.81 (t, 3H, J = 6.52 Hz) |
| 51 | 2-(3-bromobenzyl)-N-(3-(2-butylpiperidin-1-yl)propyl)-3-oxoisoindoline-5-carboxamide HCl | ¹H NMR (400 MHz, CDCl₃) δ 8.97 (s, 1H), 8.26 (s, 1H), 8.16 (d, 1H, J = 7.88 Hz), 7.41-7.48 (m, 3H), 7.19-7.25 (m, 2H), 4.78 (s, 2H), 4.31 (s, 2H), 3.63-3.76 (m, 1H), 3.47-3.50 (m, 1H), 2.96-3.03 (m, 2H), 2.20-2.42 (m, 3H), 1.16-1.93 (m, 14H), 0.83 (t, 3H, J = 6.88 Hz) |

TABLE 1-continued

| Cpd Nos | Compounds | ¹H NMR |
|---|---|---|
| 52 | 2-(4-bromobenzyl)-N-(3-(2-butylpiperidin-1-yl)propyl)-3-oxoisoindoline-5-carboxamide HCl | ¹H NMR (400 MHz, CDCl₃) δ 8.91 (s, 1H), 8.22 (s, 1H), 8.11 (d, 1H, J = 7.90 Hz), 7.43 (d, 3H, J = 8.94 Hz), 7.15 (d, 2H, J = 8.34 Hz), 4.73 (s, 2H), 4.27 (s, 2H), 3.62-3.65 (m, 1H), 3.42-3.48 (m, 1H), 2.92-2.98 (m, 2H), 2.17-2.40 (m, 3H), 1.77-1.89 (m, 1H), 1.12-1.76 (m, 13H), 0.80 (t, 3H, J = 6.87 Hz) |
| 53 | N-(3-(2-butylpiperidin-1-yl)propyl)-2-(3-iodobenzyl)-3-oxoisoindoline-5-carboxamide HCl | ¹H NMR (400 MHz, CDCl₃) δ 8.94 (s, 1H), 8.25 (s, 1H), 8.14 (d, 1H, J = 7.88 Hz), 7.64 (s, 1H), 7.61 (d, 1H, J = 7.95 Hz), 7.45 (d, 1H, J = 7.90 Hz), 7.25 (s, 1H), 7.06 (t, 1H, J = 7.76 Hz), 4.73 (s, 2H), 4.29 (s, 2H), 3.66-3.70 (m, 1H), 3.46-3.50 (m, 1H), 2.96-3.02 (m, 2H), 2.20-2.43 (m, 3H), 1.79-1.97 (m, 1H), 1.16-1.78 (m, 13H), 0.82 (t, 3H, J = 6.80 Hz) |
| 54 | N-(3-(2-butylpiperidin-1-yl)propyl)-2-(4-iodobenzyl)-3-oxoisoindoline-5-carboxamide HCl | ¹H NMR (400 MHz, CDCl₃) δ 8.92 (s, 1H), 8.25 (s, 1H), 8.14 (d, 1H, J = 7.90 Hz), 7.65 (d, 2H, J = 6.56 Hz), 7.44 (d, 1H, J = 7.94 Hz), 7.03 (d, 2H, J = 8.28 Hz), 4.73 (s, 2H), 4.28 (s, 2H), 3.66-3.70 (m, 1H), 3.44-3.50 (m, 1H), 2.98-3.01 (m, 2H), 2.16-2.45 (m, 3H), 1.81-1.94 (m, 1H), 1.15-1.81 (m, 13H), 0.82 (t, 3H, J = 6.84 Hz) |
| 55 | 2-benzyl-3-oxo-N-(3-(2-phenylpiperidin-1-yl)propyl)isoindoline-5-carboxamide HCl | ¹H NMR (400 MHz, CDCl₃) δ 8.25 (s, 1H), 8.19 (bs, 1H), 8.09 (d, 2H, J = 7.89 Hz), 7.44 (d, 1H, J = 7.91 Hz), 7.19-7.33 (m, 10H), 4.79 (s, 2H), 4.29 (s, 2H), 3.62-3.67 (m, 1H), 3.35 (d, 1H, J = 11.44 Hz), 3.10-3.15 (m, 1H), 3.00 (t, 1H, J = 7.16 Hz), 2.61-2.67 (m, 1H), 1.75-2.08 (m, 8H), 1.29-1.52 (m, 2H) |

TABLE 1-continued

| Cpd Nos | Compounds | $^1$H NMR |
|---|---|---|
| 56 | 2-(3-fluorobenzyl)-3-oxo-N-(3-(2-phenylpiperidin-1-yl)propyl)isoindoline-5-carboxamide HCl | $^1$H NMR (400 MHz, CDCl$_3$) δ 8.25 (s, 1H), 8.15 (bs, 1H), 8.11 (d, 1H, J = 7.92 Hz), 7.46 (d, 1H, J = 7.90 Hz), 7.17-7.36 (m, 6H), 7.06 (d, 1H, J = 7.62 Hz), 6.93-7.00 (m, 2H), 4.78 (s, 2H), 4.32 (s, 2H), 3.62-3.66 (m, 1H), 3.35 (d, 1H, J = 11.42 Hz), 3.06-3.17 (m, 1H), 2.99 (t, 1H, J = 7.23 Hz), 2.65 (t, 1H, J = 3.28 Hz), 1.67-2.12 (m, 8H), 1.31-1.55 (m, 2H) |
| 57 | 2-(4-fluorobenzyl)-3-oxo-N-(3-(2-phenylpiperidin-1-yl)propyl)isoindoline-5-carboxamide HCl | $^1$H NMR (400 MHz, CDCl$_3$) δ 8.26 (s, 1H), 8.19 (bs, 1H), 8.11 (d, 1H, J = 7.90 Hz), 7.47 (d, 1H, J = 7.92 Hz), 7.17-7.34 (m, 7H), 7.02 (t, 2H, J = 8.61 Hz), 4.78 (s, 2H), 4.31 (s, 2H), 3.65-3.70 (m, 1H), 3.37 (d, 1H, J = 11.52 Hz), 3.10-3.15 (m, 1H), 2.97-3.03 (m, 1H), 2.63-2.70 (m, 1H), 1.68-2.04 (m, 8H), 1.32-1.56 (m, 2H) |
| 58 | 2-(3-chlorobenzyl)-3-oxo-N-(3-(2-phenylpiperidin-1-yl)propyl)isoindoline-5-carboxamide HCl | $^1$H NMR (400 MHz, CDCl$_3$) δ 8.26 (s, 1H), 8.21 (s, 1H), 8.12 (d, 1H, J = 7.90 Hz), 7.47 (d, 1H, J = 7.91 Hz), 7.14-7.34 (m, 9H), 4.78 (s, 2H), 4.32 (s, 2H), 3.64-3.72 (m, 1H), 3.35 (d, 1H, J = 11.41 Hz), 3.04-3.17 (m, 1H), 2.94-3.04 (m, 1H), 2.62-2.68 (m, 1H), 1.68-2.13 (m, 8H), 1.32-1.56 (m, 2H) |
| 59 | 2-(4-chlorobenzyl)-3-oxo-N-(3-(2-phenylpiperidin-1-yl)propyl)isoindoline-5-carboxamide HCl | $^1$H NMR (400 MHz, CDCl$_3$) δ 8.25 (s, 1H), 8.23 (s, 1H), 8.10 (d, 1H, J = 7.90 Hz), 7.46 (d, 1H, J = 7.92 Hz), 7.15-7.34 (m, 9H), 4.76 (s, 2H), 4.30 (s, 2H), 3.62-3.71 (m, 1H), 3.35 (d, 1H, J = 11.42 Hz), 3.04-3.18 (m, 1H), 2.94-3.05 (m, 1H), 2.62-2.65 (m, 1H), 1.67-2.12 (m, 8H), 1.32-1.57 (m, 2H) |

TABLE 1-continued

| Cpd Nos | Compounds | $^1$H NMR |
|---|---|---|
| 60 | 2-(3-bromobenzyl)-3-oxo-N-(3-(2-phenylpiperidin-1-yl)propyl)isoindoline-5-carboxamide HCl | $^1$H NMR (400 MHz, CDCl$_3$) δ 8.26 (s, 1H), 8.20 (s, 1H), 8.12 (d, 1H, J = 7.91 Hz), 7.37-7.52 (m, 3H), 7.14-7.33 (m, 7H), 4.76 (s, 2H), 4.32 (s, 2H), 3.64-3.69 (m, 1H), 3.36 (d, 1H, J = 11.39 Hz), 3.09-3.15 (m, 1H), 3.00 (t, 1H, J = 7.13 Hz), 2.62-2.65 (m, 1H), 1.67-2.14 (m, 8H), 1.31-1.54 (m, 2H) |
| 61 | 2-(4-bromobenzyl)-3-oxo-N-(3-(2-phenylpiperidin-1-yl)propyl)isoindoline-5-carboxamide HCl | $^1$H NMR (400 MHz, CDCl$_3$) δ 8.25 (s, 1H), 8.20 (bs, 1H), 8.10 (d, 1H, J = 7.89 Hz), 7.43-7.48 (m, 3H), 7.14-7.29 (m, 7H), 4.74 (s, 2H), 4.30 (s, 2H), 3.63-3.68 (m, 1H), 3.35 (d, 1H, J = 11.54 Hz), 3.08-3.15 (m, 1H), 3.00 (t, 1H, J = 7.26 Hz), 2.62-2.69 (m, 1H), 1.68-2.11 (m, 8H), 1.32-1.54 (m, 2H) |
| 62 | 2-(3-iodobenzyl)-3-oxo-N-(3-(2-phenylpiperidin-1-yl)propyl)isoindoline-5-carboxamide HCl | $^1$H NMR (400 MHz, CDCl$_3$) δ 8.26 (s, 1H), 8.19 (bs, 1H), 8.13 (d, 1H, J = 7.88 Hz), 7.65 (s, 1H), 7.61 (d, 1H, J = 7.95 Hz), 7.48 (d, 1H, J = 7.91 Hz), 7.17-7.34 (m, 6H), 7.06 (t, 1H, J = 7.76 Hz), 4.74 (s, 2H), 4.32 (s, 2H), 3.65-3.70 (m, 1H), 3.36 (d, 1H, J = 11.37 Hz), 3.10-3.15 (m, 1H), 3.01 (t, 1H, J = 6.63 Hz), 2.63-2.69 (m, 1H), 1.69-2.13 (m, 8H), 1.33-1.56 (m, 2H) |
| 63 | 2-(4-iodobenzyl)-3-oxo-N-(3-(2-phenylpiperidin-1-yl)propyl)isoindoline-5-carboxamide HCl | $^1$H NMR (400 MHz, CDCl$_3$) δ 8.25 (s, 1H), 8.20 (bs, 1H), 8.11 (d, 1H, J = 7.83 Hz), 7.63 (d, 2H, J = 7.99 Hz), 7.46 (d, 1H, J = 7.91 Hz), 7.13-7.32 (m, 5H), 7.03 (d, 2H, J = 8.02 Hz), 4.73 (s, 2H), 4.29 (s, 2H), 3.65-3.69 (m, 1H), 3.50 (d, 1H, J = 11.30 Hz), 3.08-3.14 (m, 1H), 2.99 (t, 1H, J = 6.18 Hz), 2.62-2.68 (m, 1H), 1.68-2.16 (m, 8H), 1.32-1.56 (m, 2H) |

The novel compounds represented by Chemical Formula 1 in accordance with the present invention may be formulated into various dosage forms according to purpose. Illustrative, non-limiting examples of formulations containing the compounds of Chemical Formula 1 as active ingredients are given as follows.

Formulation 1: Tablet (Direct Compression)

After being sieved, 5.0 mg of the active ingredient was mixed with 14.1 mg of lactose, 0.8 mg of crospovidone USNF 0.8 mg and 0.1 mg of magnesium stearate, and directly compressed into tablets.

Formulation 2: Tablet (Wet Compression)

5.0 mg of the active ingredient was sieved and mixed with 16.0 mg of lactose and 4.0 mg of starch. To this mixture, a solution of 0.3 mg of polysorbate 80 in pure water was added in a suitable amount, followed by the formation of microparticles. The microparticles thus obtained were dried, sieved and mixed with 2.7 mg of colloidal silicon dioxide and 2.0 mg of magnesium stearate. The mixture was compressed into tablets.

Formulation 3: Powder and Capsule

After being sieved, 5 mg of the active ingredient was admixed with 14.8 mg of lactose, 10.0 mg of polyvinyl pyrrolidone and 0.2 mg of magnesium stearate. The admixture was loaded into hard No. 5 gelatin capsules using a suitable device.

Formulation 4: Injection

An injection comprising 180 mg of mannitol, 26 mg of $Na_2HPO_4.12H_2O$ and 2974 mg of distilled water in addition to 100 mg of the active ingredient was prepared.

Meanwhile, the novel compounds of Chemical Formula 1 in accordance with the present invention were assayed for antagonistic activity against T-type calcium channels. In this regard, an examination was made of the % inhibition of the compounds against T-type calcium channel using FDSS6000. Some of them which were found to have excellent inhibitory activity were assessed for $IC_{50}$ with the aid of an automated patch clamp technique.

In the present invention, in order to search for an efficient inhibitor against T-type calcium channel, a primary assay for T-type calcium channel inhibiting activity was conducted by a high-efficient assay using FDSS6000, wherein mammal HEK293 cell lines (originated from human kidney carcinoma cells), which specifically express aIG of T-type calcium channel, were used for the primary assay.

Through the primary assay, compounds which showed meaningful inhibitive effects were selected. The selected compounds were used in a second assay for T-type calcium channel inhibiting activity using electrophysiological whole cell patch clamp method, wherein mammal HEK293 cell lines, which are originated from human kidney carcinoma cells and which specifically express aIG of T-type calcium channel, were used for the second assay. As a reference drug, mibefradil which had been developed as T-type calcium channel inhibitor was used.

EXPERIMENTAL EXAMPLES

Experimental Example 1

Assay for Inhibitory Activity against T-type Calcium Channel using FDSS6000

HEK293 cells which stably express both $\alpha_{1G}$ and Kir2.1 subunits [1] were grown in Dulbecoo's modified Eagle's medium supplemented with 10% (v/v) fetal bovine serum, penicillin (100 U/ml), streptomycin (100 □g/ml), geneticin (500 □g/ml), and puromycin (1 μg/ml) at 37° C. in a humid atmosphere of 5% $CO_2$ and 95% air. Cells were seeded into 96-well black wall clear bottom plates at a density of 40,000 cells/well and were used on the next day for high-throughput screening (HTS) FDSS6000 assay [2]. For FDSS6000 assay, cells were incubated for 60 min at room temperature with 5 □M fluo3/AM and 0.001% Pluronic F-127 in a HEPES-buffered solution composed of (in MM): 115 NaCl, 5.4 KCl, 0.8 $MgCl_2$, 1.8 $CaCl_2$, 20 HEPES, 13.8 glucose (pH 7.4). During fluorescence-based FDSS6000 assay, $\square_{1G}$ T-type $Ca^{2+}$ channels were activated using a high concentration of KCl (70 mM) in 10 mM $CaCl_2$ contained HEPES-buffered solution, and the increase in $[Ca^{2+}]_i$ by KCl-induced depolarization was detected. All data were collected and analyzed using FDSS6000 and related software (Hamamatsu, Japan).

Experimental Example 2

Measurement of Ion Currents Through T-Type Calcium Channel Activity Using Automated Patch Clamp 1. Cell Culture and Preparation Stably expressed T-type calcium channels in Human Embryonic Kidney (HEK)-293 cell were provided by Korea Research Institute of Bioscience and Biotechnology (KRIBB) and hERG (human ether-a-go-go-related gene) channels induced by a Tet-expression system expressed in HEK-293 cell were purchased from Iongate (Frankfurt, Germany). In a humidified 5% $CO_2$ incubator at 37° C., T-type calcium channel expressed cells were maintained in Dulbecco's modified Eagle's medium (DMEM) including 10% Fetal Bovine Serum (FBS), and hERG channel expressed cells were maintained in MEM with 10% FBS. For hERG channel expression, the Tet-expression system was activated by adding 1 μg/ml Doxycyclin into the hERG channel cell growth medium 20 h prior to use. Cell lines were subcultured once in three days and used for patch clamp recordings at final confluence of 50-80%. To harvest cells, cell detacher, Trypsin-EDTA (0.25×) was added into the dish and single cells were made using a pipette. Trypsin was removed by centrifugation at 1100 rpm for 3 min. Cells were automatically suspended after adding external cellular solution at room temperature.

2. Solution and Drugs

The composition of solution for measuring T-type calcium channel and hERG channel activity is following: 140 mM NaCl, 2 mM $CaCl_2$, 4 mM KCl, 1 mM $MgCl_2$, 5 mM D-glucose and 10 mM HEPES (pH 7.4) for external cellular solution, 50 mM KCl, 10 mM NaCl, 60 mM KF, 2 mM $MgCl_2$, 10 mM HEPES and 20 mM EGTA (pH 7.2) for internal cellular solution and 80 mM NaCl, 35 mM $CaCl_2$, 3 mM KCl, 10 mM $MgCl_2$ and 10 mM HEPES (pH 7.4) for seal enhancer. T-type calcium channel activity was recorded after adding 10 mM $Ba^{2+}$ into external solution. Each compound dissolved in 100% DMSO with a final concentration of 100 mM was diluted to 10 nM~100 μM range in external solution with 10 mM $Ba^{2+}$ for T-type calcium channel and no $Ba^{2+}$ for hERG channel recordings.

3. Electrophysiology and Data Analysis

In all experiments, auto patch clamp machine NPC©-16 Patchliner (Nanion Technologies, Germany) and whole-cell patch clamp technique were used. Channel current was recorded by EPC10 (HEKA, Germany) amplifier. Cell suspension and patch solutions were automatically divided into the chip (NPC-16 Chip, Nanion Technologies, Germany). Inward current was recorded at −20 mV depolarization potential at intervals of 10 s during 300 ms with −100 mV holding potential for T-type calcium channels, and tail current was recorded at −50 mV at intervals of 10 s during 500 ms after 20 mV depolarization during 200 ms with −80 mV holding potential for hERG channels. Compounds at each concentration were applied to the cell during 20 s. Inhibition curves and $IC_{50}$ values were automatically calculated from peak currents using data analysis program, IGOR Pro (WaveMetrics, USA).

The results are summarized in Table 2, below.

TABLE 2

Antagonistic Activity against T-Type Calcium Channel

| Compound | FDSS (% Inhibition, at 10 μM) | $IC_{50}$ (μM) |
|---|---|---|
| Compound 1 | 21.97 | 9.57 |
| Compound 7 | 33.43 | 9.77 |
| Compound 24 | 46.03 | 4.07 |
| Compound 33 | 60.81 | 1.74 |
| Compound 36 | 53.82 | 6.87 |
| Compound 40 | 56.71 | 1.01 |
| Compound 42 | 44.40 | 4.15 |
| Compound 43 | 51.69 | 5.1 |
| Compound 44 | 60.66 | 4.36 |
| Compound 45 | 58.87 | 1.07 |
| Compound 46 | 55.30 | 2.65 |
| Compound 47 | 49.03 | 2.3 |
| Compound 48 | 62.10 | 1.92 |
| Compound 49 | 71.78 | 0.62 |
| Compound 60 | 55.20 | 1.54 |
| Compound 61 | 45.63 | 1.07 |

As apparent from data of Table 2, the compounds according to the present invention range in $IC_{50}$ from 0.62 to 9.77 μM, showing excellent inhibitory activity against T-type calcium channel, and thus can be useful in the prevention or treatment of T-type calcium channel-related diseases, such as hypertension, cancer, epilepsy, neuropathic pain, etc.

With inhibitory activity against T-type calcium channel, as described hitherto, the novel isoindolinone derivatives of Chemical Formula 1 in accordance with the present invention may be effectively used as preventatives or therapeutics for T-type calcium channel-related diseases, such as hypertension, cancer, epilepsy, neuropathic pain, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An isoindolinone compound, represented by the following Chemical Formula 1, or a pharmaceutically acceptable salt thereof:

[Chemical Formula 1]

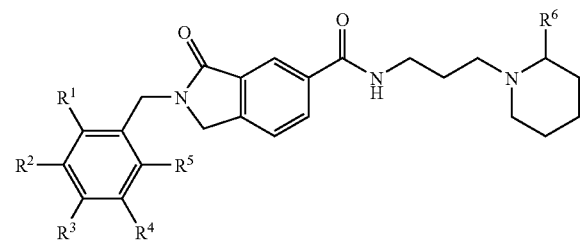

wherein, $R^1$~$R^5$ represent independently a hydrogen atom, a halogen atom, a $C_1$~$C_6$ alkoxy, a $C_1$~$C_6$ alkyl, a $C_1$~$C_6$ haloalkyl, a nitro, a cyano or a hydroxy; and $R^6$ represents a hydrogen atom, a $C_1$~$C_6$ alkyl, or an aryl.

2. The isoindolinone compound or the pharmaceutically acceptable salt according to claim 1, wherein $R^1$~$R^5$ are a hydrogen atom or a halogen atom selected from a group consisting of a fluorine atom, a chlorine atom, a bromine atom, an iodine atom and a combination thereof; and $R^6$ is a hydrogen atom, a methyl, an ethyl, a normal propyl, an isopropyl, a normal butyl, a tert-butyl or a phenyl.

3. The isoindolinone compound or the pharmaceutically acceptable salt according to claim 1, wherein the idoindoline compound is selected from a group consisting of:

(1) 2-benzyl-3-oxo-N-(3-(piperidin-1-yl)propyl)isoindoline-5-carboxamide;
(2) 2-(3-fluorobenzyl)-3-oxo-N-(3-(piperidin-1-yl)propypisoindoline-5-carboxamide,
(3) 2-(4-fluorobenzyl)-3-oxo-N-(3-(piperidin-1-yl)propyl)isoindoline-5-carboxamide;
(4) 2-(3-chlorobenzyl)-3-oxo-N-(3-(piperidin-1-yl)propyl)isoindoline-5-carboxamide;
(5) 2-(4-chlorobenzyl)-3-oxo-N-(3-(piperidin-1-yl)propyl)isoindoline-5-carboxamide;
(6) 2-(3-bromobenzyl)-3-oxo-N-(3-(piperidin-1-yl)propyl)isoindoline-5-carboxamide;
(7) 2-(4-bromobenzyl)-3-oxo-N-(3-(piperidin-1-yl)propyl)isoindoline-5-carboxamide;
(8) 2-(3-iodobenzyl)-3-oxo-N-(3-(piperidin-1-yl)propyl)isoindoline-5-carboxamide;
(9) 2-(4-iodobenzyl)-3-oxo-N-(3-(piperidin-1-yl)propyl)isoindoline-5-carboxamide;
(10) 2-benzyl-N-(3-(2-methylpiperidin-1-yl)propyl)-3-oxoisoindoline-5-carboxamide;
(11) 2-(3-fluorobenzyl)-N-(3-(2-methylpiperidin-1-yl)propyl)-3-oxoisoindoline-5-carboxamide;
(12) 2-(4-fluorobenzyl)-N-(3-(2-methylpiperidin-1-yl)propyl)-3-oxoisoindoline-5-carboxamide;
(13) 2-(3-chlorobenzyl)-N-(3-(2-methylpiperidin-1-yl)propyl)-3-oxoisoindoline-5-carboxamide;
(14) 2-(4-chlorobenzyl)-N-(3-(2-methylpiperidin-1-yl)propyl)-3-oxoisoindoline-5-carboxamide;
(15) 2-(3-bromobenzyl)-N-(3-(2-methylpiperidin-1-yl)propyl)-3-oxoisoindoline-5-carboxamide;
(16) 2-(4-bromobenzyl)-N-(3-(2-methylpiperidin-1-yl)propyl)-3-oxoisoindoline-5-carboxamide;
(17) 2 (3-iodobenzyl)-N-(3-(2-methylpiperidin-1-yl)propyl)-3-oxoisoindoline-5-carboxamide;
(18) 2-(4-iodobenzyl)-N-(3-(2-methylpiperidin-1-yl)propyl)-3-oxoisoindoline-5-carboxamide;
(19) 2-benzyl-N-(3-(2-ethylpiperidin-1-yl) propyl) -3oxoisoindoline-5-carboxamide;
(20) N-(3-(2-ethylpiperidin-1-yl)propyl)-2-(3fluorobenzyl)-3-oxoisoindoline-5-carboxamide;
(21) N-(3-(2-ethylpiperidin-1-yl)propyl)-2-(4fluorobenzyl)-3-oxoisoindoline-5-carboxamide;
(22) 2-(3-chlorobenzyl)-N-(3-(2-ethylpiperidin-1-yl)propyl)-3-oxoisoindoline-5-carboxamide;
(23) 2-(4-chlorobenzyl)-N-(3-(2-ethylpiperidin-1-yl)propyl)-3-oxoisoindoline-5-carboxamide;
(24) 2-(3-bromobenzyl)-N-(3-(2-ethylpiperidin-1-yl)propyl)-3-oxoisoindoline-5-carboxamide;
(25) 2-(4-bromobenzyl)-N-(3-(2-ethylpiperidin-1-yl)propyl)-3-oxoisoindoline-5-carboxamide;
(26) N-(3-(2-ethylpiperidin-1-yl)propyl)-2-(3iodobenzyl)-3-oxoisoindoline-5-carboxamide;
(27) N-(3-(2-ethylpiperidin-1-yl)propyl)-2-(4iodobenzyl)-3-oxoisoindoline-5-carboxamide;

(28) 2-benzyl-3-oxo-N-(3-(2-propylpiperidin-1-yl)propyl)isoindoline-5-carboxamide;
(29) 2-(3-fluorobenzyl) -3-oxo-N-(3-(2-propylpiperidin-1-yl)propyl)isoindoline-5-carboxamide,
(30) 2-(4-fluorobenzyl)-3-oxo-N-(3-(2-propylpiperidin-1-yl)propyl)isoindoline-5-carboxamide;
(31) 2-(3-chlorobenzyl)-3-oxo-N-(3-(2-propylpiperidin-1-yl)propyl)isoindoline-5-carboxamide;
(32) 2-(4-chlorobenzyl)-3-oxo-N-(3-(2-propylpiperidin-1-yl)propyl)isoindoline-5-carboxamide;
(33) 2-(3-bromobenzyl)-3-oxo-N-(3-(2-propylpiperidin-1-yl)propyl)isoindoline-5-carboxamide;
(34) 2-(4-bromobenzyl) -3-oxo-N-(3-(2-propylpiperidin-1-yl)propyl)isoindoline-5-carboxamide;
(35) 2-(3-iodobenzyl)-3-oxo-N-(3-(2-propylpiperidin-1-yl)propyl)isoindoline-5-carboxamide;
(36) 2-(4-iodobenzyl)-3-oxo-N-(3-(2-propylpiperidin-1-yl)propyl)isoindoline-5-carboxamide;
(37) 2-benzyl-N-(3-(2-isopropylpiperidin-1-yl)propyl)-3-oxoisoindoline-5-carboxamide,
(38) 2-(3-fluorobenzyl)-N-(3-(2-isopropylpiperidin-1-yl)propyl)-3-oxoisoindoline-5-carboxamide;
(39) 2-(4-fluorobenzyl) -N-(3-(2-isopropylpiperidin-1-yl)propyl)-3-oxoisoindoline-5-carboxamide;
(40) 2-(3-chlorobenzyl)-N-(3-(2-isopropylpiperidin-1-yl)propyl)-3-oxoisoindoline-5-carboxamide;
(41) 2-(4-chlorobenzyl)-N-(3-(2-isopropylpiperidin-1-yl)propyl)-3-oxoisoindoline-5-carboxamide;
(42) 2-(3-bromobenzyl)-N-(3-(2-isopropylpiperidin-1-yl)propyl)-3-oxoisoindoline-5-carboxamide;
(43) 2-(4-bromobenzyl)-N-(3-(2-isopropylpiperidin-1-yl)propyl)-3-oxoisoindoline-5-carboxamide;
(44) 2-(3-iodobenzyl) -N-(3-(2-isopropylpiperidin-1-yl)propyl)-3-oxoisoindoline-5-carboxamide;
(45) 2-(4-iodobenzyl)-N-(3-(2-isopropylpiperidin-1-yl)propyl)-3-oxoisoindoline-5-carboxamide;
(46) 2-benzyl-N-(3-(2-butylpiperidin-1-yl)propyl)-3-oxoisoindoline-5-carboxamide;
(47) N-(3-(2-butylpiperidin-1-yl)propyl)-2-(3-fluorobenzyl)-3-oxoisoindoline-5-carboxamide;
(48) N-(3-(2-butylpiperidin-tyl)propyl)-2-(4-fluorobenzyl)-3-oxoisoindoline-5-carboxamide;
(49) N-(3-(2-butylpiperidin-1-yl)propyl)-2-(3-chlorobenzyl)-3-oxoisoindoline-5-carboxamide;
(50) N-(3-(2-butylpiperidin-1-yl)propyl)-2-(4-chlorobenzyl)-3-oxoisoindoline-5-carboxamide;
(51) 2-(3-bromobenzyl)-N-(3-(2-butylpiperidin-1-yl)propyl)-3-oxoisoindoline-5-carboxamide;
(52) 2-(4-bromobenzyl)-N-(3-(2-butylpiperidin-1-yl)propyl)-3-oxoisoindoline-5-carboxamide;
(53) N-(3-(2-butylpiperidin-1-yl)propyl)-2-(3iodobenzyl)-3-oxoisoindoline-5-carboxamide;
(54) N-(3-(2-butylpiperidin-1-yl)propyl)-2-(4iodobenzyl)-3-oxoisoindoline-5-carboxamide;
(55) 2-benzyl-3-oxo-N-(3-(2-phenylpiperidin-1-yl)propyl)isoindoline-5-carboxamide;
(56) 2-(3-fluorobenzyl)-3-oxo-N-(3-(2-phenylpiperidin-1-yl)propyl)isoindoline-5-carboxamide;
(57) 2-(4-fluorobenzyl)-3-oxo-N-(3-(2-phenylpiperidin-1-yl)propyl)isoindoline-5-carboxamide,
(58) 2-(3-chlorobenzyl)-3-oxo-N-(3-(2-phenylpiperidin-1-yl)propyl)isoindoline-5-carboxamide;
(59) 2-(4-chlorobenzyl)-3-oxo-N-(3-(2-phenylpiperidin-1-yl)propyl)isoindoline-5-carboxamide;
(60) 2-(3-bromobenzyl)-3-oxo-N-(3-(2-phenylpiperidin-1-yl)propyl)isoindoline-5-carboxamide;
(61) 2-(4-bromobenzyl)-3-oxo-N-(3-(2-phenylpiperidin-1-yl)propyl)isoindoline-5-carboxamide;
(62) 2-(3-iodobenzyl)-3-oxo-N-(3-(2-phenylpiperidin-1-yl)propyl)isoindoline-5-carboxamide; and
(63) 2-(4-iodobenzyl)-3-oxo-N-(3-(2-phenylpiperidin-1-yl)propyl)isoindoline-5-carboxamide.

4. A method for preparing the isoindolinone compound of Chemical Formula 1, as illustrated in the following Reaction Scheme I, comprising:
converting 3-bromo-4-methylbenzoic acid of Chemical Formula 2 into aryl lithium using methylmagnesium bromide ($CH_3MgBr$) and n-butyl lithium under nitrogen atmosphere, followed by the carboxylation of the aryl lithium with carbon dioxide into a dicarboxylic acid of Chemical Formula 3 (Step 1);
esterifying the dicarboxylic acid of Chemical Formula 3 with an alkyl to give a diester compound of Chemical Formula 4 (Step 2);
brominating the diester of Chemical Formula 4 into a bromine compound of Chemical Formula 5 (Step 3);
subjecting the brominated compound of Chemical Formula 5 to $SN_2$-type alkylation with a benzyleamine compound of Chemical Formula 6, followed by cyclization to afford an isoindolinone backbone compound of Chemical Formula 7 (Step 4);
hydrolyzing the compound of Chemical Formula 7 to an isoindolinone carboxylic acid derivative of Chemical Formula 8 (Step 5); and
amide-coupling the isoindolinone carboxylic acid of Chemical Formula 8 with a piperidinyl propylamine compound of 5 Chemical Formula 9 to afford the isoindolinone compound of Chemical Formula 1 (Step 6)

[Reaction Scheme 1]
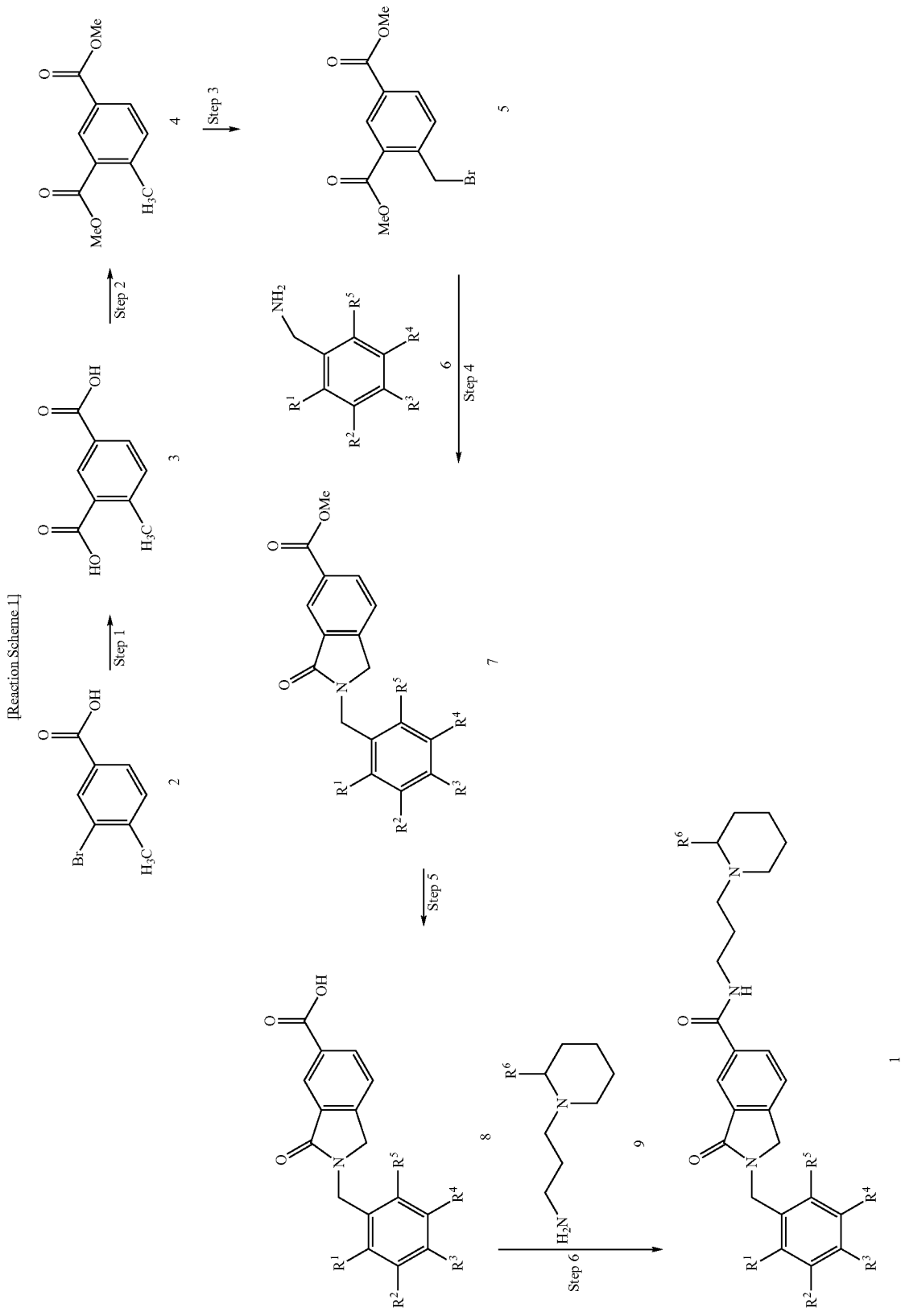

wherein $R^1$~$R^6$ are as defined in claim 1.

5. The isoindolinone compound or the pharmaceutically acceptable salt according to claim 1, wherein the pharmaceutically acceptable salt is formed from a free acid.

6. The isoindolinone compound or the pharmaceutically acceptable salt according to claim 5, wherein the free acid is selected from the group consisting of hydrochloric acid, bromic acid, sulfonic acid, aminosulfuric acid, phosphoric acid, nitric acid, acetic acid, propionic acid, succinic acid, glycolic acid, stearic acid, lactic acid tartaric acid, citric acid, ρ-toluenesulfonic acid, and methanesulfonic acid.

* * * * *